(12) United States Patent
Kaiser et al.

(10) Patent No.: US 10,501,644 B2
(45) Date of Patent: *Dec. 10, 2019

(54) REACTIVE SURFACE COATING HAVING CHEMICAL DECONTAMINATION AND BIOCIDAL PROPERTIES

(71) Applicant: AMERICAN STERILIZER COMPANY, Mentor, OH (US)

(72) Inventors: Herbert J. Kaiser, Pontoon Beach, IL (US); Miranda C. Shaver, Saint Louis, MO (US); Timothy Lee Giddens, Florissant, MO (US)

(73) Assignee: AMERICAN STERILIZER COMPANY, Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/009,745

(22) Filed: Jun. 15, 2018

(65) Prior Publication Data

US 2018/0291212 A1 Oct. 11, 2018

Related U.S. Application Data

(62) Division of application No. 15/142,333, filed on Apr. 29, 2016, now Pat. No. 10,017,650, which is a division of application No. 13/836,364, filed on Mar. 15, 2013, now Pat. No. 9,353,269.

(51) Int. Cl.
| | |
|---|---|
| C09D 5/14 | (2006.01) |
| A01N 59/00 | (2006.01) |
| A01N 59/06 | (2006.01) |
| C09D 139/06 | (2006.01) |
| A62D 5/00 | (2006.01) |
| B05D 1/02 | (2006.01) |
| B05D 1/28 | (2006.01) |
| B05D 3/00 | (2006.01) |

(52) U.S. Cl.
CPC .............. *C09D 5/14* (2013.01); *A01N 59/00* (2013.01); *A01N 59/06* (2013.01); *A62D 5/00* (2013.01); *B05D 1/02* (2013.01); *B05D 1/28* (2013.01); *B05D 3/007* (2013.01); *C09D 139/06* (2013.01)

(58) Field of Classification Search
CPC ...... C08L 39/06; C08L 2203/16; C08L 23/06; C08L 23/30; A01N 25/10; A01N 59/00; A01N 59/12; A01N 25/34; C08F 10/02; C08F 26/10; C08F 126/10; C08F 226/10; C08K 3/015
See application file for complete search history.

(56) References Cited

U.S. PATENT DOCUMENTS

| | | | |
|---|---|---|---|
| 3,376,110 A | 4/1968 | Shiraeff | |
| 3,480,557 A | 11/1969 | Shiraeff | |
| 3,626,025 A | 12/1971 | Anspon | |
| 4,076,656 A | 2/1978 | White et al. | |
| 5,077,047 A | 12/1991 | Biss et al. | |
| 5,130,124 A * | 7/1992 | Merianos | A01N 59/00 424/53 |
| 5,587,191 A | 12/1996 | Donsbach et al. | |
| 6,811,771 B1 | 11/2004 | Sugo et al. | |
| 7,306,777 B2 | 12/2007 | Bringley et al. | |
| 7,449,194 B2 | 11/2008 | Lelah et al. | |
| 7,659,344 B2 * | 2/2010 | Urian | A01N 59/12 264/464 |
| 7,674,837 B2 | 3/2010 | Gaserod et al. | |
| 8,124,169 B2 | 2/2012 | Ylitalo et al. | |
| 8,217,220 B2 | 7/2012 | Berland et al. | |
| 2005/0089821 A1 * | 4/2005 | Allred | A61C 19/063 433/215 |
| 2005/0115197 A1 | 6/2005 | Meyers et al. | |
| 2005/0137272 A1 | 6/2005 | Gaserod et al. | |
| 2008/0138373 A1 | 6/2008 | Liu et al. | |
| 2008/0260026 A1 | 10/2008 | Harumatsu | |
| 2009/0155451 A1 * | 6/2009 | Ylitalo | A01N 25/10 427/8 |
| 2009/0275906 A1 * | 11/2009 | Berland | A61L 15/225 604/359 |
| 2010/0009011 A1 | 1/2010 | Arlt et al. | |
| 2010/0240799 A1 | 9/2010 | Hofmann et al. | |
| 2011/0293540 A1 | 12/2011 | Musa et al. | |
| 2012/0301522 A1 | 11/2012 | Prosise et al. | |

FOREIGN PATENT DOCUMENTS

WO   2006135620 A1   12/2006

* cited by examiner

*Primary Examiner* — Robert C Boyle
(74) *Attorney, Agent, or Firm* — Hudak, Shunk & Farine Co. LPA

(57) ABSTRACT

Reactive compositions are provided, having biocidal and chemical decontamination/neutralization properties, comprising a hygroscopic polymer and an active, which are useful in a variety of commercial, healthcare and military applications and a wide variety of contaminants, including without limitation chemical and biological warfare agents. The reactive compositions are renewable or rechargeable after use by exposure to an additional application of the active and do not require removal, disposal or replacement of the originally applied composition. Methods for preparing and applying the reactive compositions are disclosed.

4 Claims, 22 Drawing Sheets

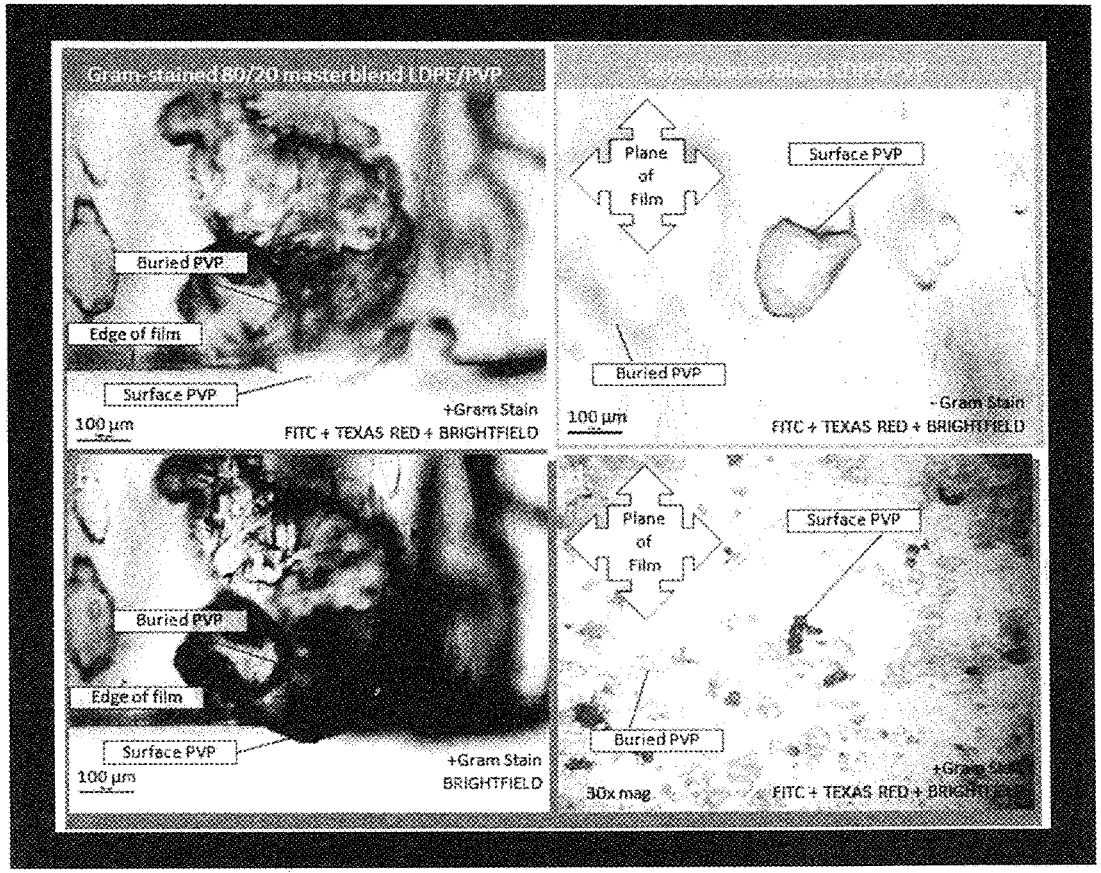

a. Gram-stained LDPE/PVP 80/20 blend 'master blend' film (film) composite image. Viewing the edge of the film, with a partially exposed embedded PVP kernel extending beyond the film edge. Green – FITC fluorescence, RED – TEXAS RED fluorescence. 100x magnification. b. Identical view as (a.), in brightfield illumination. Pink/purple – Gram stain. 100x. c. Composite image of film without stain. Center kernel 'Surface PVP' is above the plane of the film. Green shadowing is 'buried PVP'. Green – FITC fluorescence, RED – TEXAS RED fluorescence (missing). 100x magnification. d. Gram-stained film featuring the distinction between surface PVP available for staining and buried PVP unavailable for staining, and the arrangement of these two types. Pink/purple – Gram stain. ~30x magnification.

FIG. 18

REACTIVE SURFACE COATING HAVING CHEMICAL DECONTAMINATION AND BIOCIDAL PROPERTIES

The U.S. Government may have certain rights in this invention under U.S. Army Natick Solider Systems Center contracts W911SR-07-C-0067 and W911SR-09-C-003.

FIELD OF THE INVENTION

This invention is directed to a reactive coating composition for surfaces and articles, which has the ability to reduce or eliminate microbial contamination and/or to neutralize chemical agents. The reactive coating comprises a polymer and an active. Uniquely, the reactive composition may be renewed or recharged by reapplication of the active. The invention is also directed to methods for providing a reactive coating to a surface or articles.

BACKGROUND OF THE INVENTION

The U.S. armed forces have a need to operate, survive and sustain operations safely in chemical and biological hazard environments. The continued proliferation of chemical and biological weapons creates a need to ensure that U.S. forces can successfully complete missions in environments that could become contaminated with chemical and biological agents. Technologies are needed to support the soldier across the spectrum of potential conflicts and contaminant exposures. In addition, other environments, particularly in healthcare facilities, have a need to operate and to sustain operations in areas that are exposed to chemical and biological contaminant challenges on a daily basis.

Current decontamination/cleaning methods for biological and chemical contaminants are laborious and are greatly dependent on the care and attention to detail of cleaning personnel. Traditionally, these methods require the use of hazardous chemicals and generally do not provide long-lasting or ongoing protection. Once a surface has been manually cleaned, new contaminants on the surface can present a threat to the health and safety of those who come in contact it until the next manual cleaning procedure.

In military applications in particular, operational decontamination requires that an object or device be enabled to return to service as rapidly as possible; thorough decontamination enables an object or device to be handled by any user without personal protective equipment. Both operational and thorough decontamination are advantages that may be achieved with reactive coating compositions of the invention.

Reactive coatings have been in development for a number of years with some limited success. Reactive coatings with the capacity to decontaminate smaller areas or articles and/or smaller amounts of chemical and biological agents have been demonstrated. Traditionally, due to limits on the amount of "reactivity" that can be applied to a surface or incorporated into an article, reactive coatings alone are unlikely to have the capacity to effect operational or thorough decontamination of larger surface areas heavily contaminated with chemical or biological warfare agents.

A reactive coating with the ability to reduce, eliminate or neutralize contamination between cleanings provides significant benefits. Most currently available reactive coating technologies are considered "permanent" in the sense that when integrated into a fabric or substrate material or applied to a surface, they remain continuously reactive until fouled by contaminants. At that point, the material or surface usually must be thoroughly cleaned and decontaminated, or removed, disposed of, and replaced.

By contrast, a renewable coating is a two-part system consisting of first, a nonreactive foundation layer that may be either integrated into a substrate or applied as a surface coating, and second, an activation chemistry (liquid or gaseous), or "active", that renders the foundation layer "reactive" to a contaminant on the surface. The reactivity of a renewable coating may be "recharged" or renewed by reapplication of the active after exposure to chemical and biological contaminants. Ideally, there would be no need to thoroughly clean or decontaminate, remove, dispose of, and replace the foundation layer of a renewable coating.

Renewable coatings, in particular, offer a potential solution to problems typically encountered with traditional reactive surface technologies. These include: fouling from environmental contaminants, limited reactive capacity at the surface and rapid deterioration of the surface from environmental conditions or continuous exposure to contaminants.

In general, chemicals used against biological species and chemical contaminants are classified as "actives" and include without limitation halides, oxidizers, phenols, quaternary ammonium salts, heavy metals, and aldehydes. When higher levels of actives are present and available on the surface, decontamination efficacy will improve. Commercially, actives have been added to surfaces in order to try and create reactive and time-release materials. Two currently available examples are HALOSHIELD, a slow release chlorine-based system for making antimicrobial textiles, and TRIOSYN, a quaternary ammonium triodide coating. HALOSHIELD-treated textiles rely on replacement of chlorine from bleach when being washed.

Attempts to create antimicrobial coatings for surfaces and articles are described in the literature and have met with some limited success. U.S. Pat. No. 7,306,777 is directed to a polyethylene/polyvinyl alcohol copolymer comprising a metal based antimicrobial compositions within the polymer for application to a variety of substrates. The copolymer is not stated to be renewable.

U.S. Pat. No. 7,449,194 is directed to a "body covering" article (such as an apron, gown or glove) that is made from an antimicrobial material. The antimicrobial material comprises a polymer, such as polyolefins, PVC, latex, nitrile, mylar, polyurethane and neoprene; a plasticizer; and an active capable of generating and releasing at least one gas upon exposure to light and/or humidity. The gas is antimicrobial and will retard, control, kill or prevent microbiological contamination of the skin or other surface in contact with the article. The "gas generating" composition includes hydrogen peroxide (0.5-20 wt. %), chlorine dioxide, sulfur dioxide, carbon dioxide and nitrous oxide. The article is not renewable or rechargeable with active.

U.S. Patent Publication No. 2008/0138373 is directed to a protective or cleaning article that has an exterior surface of at least a partial coating or layer of a stabilized peroxide compound and a treatment for protective articles and cleaning articles, such as tissues and gloves. Hydrogen peroxide and other peroxide salts are listed as oxidizing antimicrobials thought to be virucidal as well as bactericidal. Vinyl pyrrolidone copolymers are mentioned as hydrogen peroxide stabilizing agents; however, vinyl pyrrolidone homopolymers are not acceptable because they create stiff films. Preferable vinyl pyrrolidone copolymers are those that do not form films or form only soft films. The treatment is not described as renewable.

U.S. Patent Publication No. US2008/00260026 discloses a "removable" coating comprising a water soluble polymer (that will dry to form a film) and at least one antimicrobial. The composition is described as biocidal and/or biostatic. Polyvinyl alcohols alone or copolymerized with olefins are disclosed. Peroxide and peroxyacids are disclosed as actives, among many other actives disclosed. The coating is not stated to be renewable and may or may not be biocidal.

U.S. Patent Publication No. 2009/0155451 discloses an antimicrobial coating system, comprising a film-forming composition and an antimicrobial. The film-forming composition comprises a polymer and includes an effective amount of an antimicrobial agent dispersed within the polymer. The polymer may be an acrylic, urethane or PVA polymer; the active is selected from fatty acid monoesters, fatty acid monoethers, a transition metal ion-containing compound, a quaternary ammonium compound, a biguanide, or combinations thereof. Peroxides are identified only as fast-acting optional components that do not provide activity over extended periods of time, as compared to the antimicrobial agent. The coating is not renewable.

U.S. Patent Publication No. 2009/0275906 discloses an absorbent article with a thin film layer that includes an active agent. Peroxide is one of the "actives" disclosed. The thin film is polymeric and is layered onto the article using LBL deposition. PVP comprises one of the "layers", i.e., the second "neutral" layer that is a hydrogen bond acceptor. The "first" layer includes other polymers that are hydrogen bond donors. Claims are directed to the absorbent article, not the film. There is no mention that the absorbent article may be renewed or recharged with active.

U.S. Patent Publication No. 2010/0009011 is directed to a polyurethane-based composition containing crosslinked polymers of heterocyclic N-vinyl monomers (including PVP, 0.1-100% by wt.). The composition is used to make sponges or other objects that release disinfectants over time. Hydrogen peroxide (3-70 wt. %) is one of the potential disinfectants. The publication is concerned with foam based articles and not coatings. The disinfectant activity is not renewable.

WO 2006/135620 is directed to a PVP/hydrogen peroxide complex used to form a gel that is used to deodorize air and surfaces. The active could also be a peroxohydrate compound. The complex relies on release of gas to deodorize air and surfaces. It may be used as a solution, solid, gel, or contained within a device.

The literature shows that while there has been a lot of activity in developing antimicrobial textiles, absorbent sponges, tissues, and other articles, no current reactive surface technology has been developed that has demonstrated efficacy sufficient to decontaminate standard or larger scale interior or exterior chemical or biological challenges, particularly those encountered with chemical and biological warfare agents. No current technologies are available for field military use as a reactive coating. Most activity has surrounded the development of single-use reactive surfaces and articles that must be thoroughly cleaned and decontaminated, or removed, disposed of and replaced after contamination. No current technologies have been demonstrated to be renewable with simple reapplication of the active.

Significant effort has been invested into the creation of reactive surfaces for larger scale commercial and military use with limited progress. Most technologies under development suffer from a variety of performance challenges but most notably the following:

Limited capacity—many technologies have been shown to be biostatic (only prevent growth) under ideal conditions. Many current systems require an extended amount of time (days) before they can fully deal with a realistic level of contamination. Ideally, a reactive surface would provide a very high level of activity against bacteria, viruses, and fungi and even hard to kill spores. Additionally, the ideal system would also reduce the threats from chemical warfare agents or other toxic chemicals.

Cross-contamination—biostatic technologies only protect the surface they are applied to. This approach leaves contaminant available for transfer to any surface or entity that comes into contact. The ideal system would inactivate the biological or chemical contaminant assuring a safe surface between cleaning.

Fouling—a well-known problem for reactive coatings is fouling of the surface by either environmental conditions or residue from the contaminant that has been neutralized. Actives that are available on a clean surface can easily be covered by layers of simple dirt/dust or they can be covered by the residue from decontaminated biologicals or chemicals. An ideal system would be resistant to a reduction in performance resulting from these organic loads.

Practical, multiple use applications—many of the current technologies are designed for specific applications under ideal conditions and are therefore limited in their viability.

There is, therefore, a need for reactive surface technology that provides biocidal activity and chemical decontamination even in the face of organic load buildup, that is effective against a wide variety of contaminants and that can be applied to a wide variety of surfaces in traditional interior and exterior environments. There is no current consensus as to performance requirements for reactive surface coatings. An ideal system would be applicable to commercial (including medical) and military markets, safe to use and handle, effective against a wide variety of contaminants, applicable to and easily integrated onto or into a wide variety of porous and non-porous surfaces, effective under organic load buildup, and renewable or rechargeable by reapplication of the active. In addition, a useful system would be stable and have extended use life and be flexible in its application, giving the user the option to activate the film in a number of ways using different forms of the active.

A new technology has been developed comprising a reactive surface designed to work in conjunction with current decontamination systems and processes to achieve greater efficacy, or as a stand-alone product to address residual or low levels of agent. This technology surprisingly meets the need for the quick restoration of equipment, vehicles, building and shelter interiors, and essential support functions, such as field based military facilities, hospitals, manufacturing facilities and other facilities exposed to chemical and biological challenges.

A key advantage of this technology aligns with certain military requirements to sustain combat operations through 1) the ability to quickly bring forces back to full operational effectiveness; 2) restoring equipment and vehicles to usable status quickly; and 3) reducing the logistics burden of decontamination operations.

This invention is directed to a reactive surface coating composition that may be incorporated into or onto a surface or material as part of the manufacturing process or applied to an existing material at any point during its life. The surfaces to which this invention can be applied are unlimited. This invention has been demonstrated to be effective when applied to both hard non-porous surfaces and porous surfaces.

The inventive reactive surface compositions are comprised primarily of a hygroscopic polymer or blend of polymers (hereinafter referred to as the polymer) and an active. The ability to modify the physical properties of the inventive reactive surface compositions to tailor them for various purposes is an unexpected and distinct advantage of the invention.

The polymer selected for use in the inventive compositions may have and preferably has a synergistic effect with an active(s), such as, but not limited to, hydrogen peroxide, chlorine, peracetic acid, and the like. This synergistic effect is demonstrated as an increase in biocidal or chemical decontamination activity that is greater than that achieved with either the polymer or the active when used alone. Importantly, upon mixing with or exposure to the active, the selected polymer does not reduce or limit the amount of active available for the application or its efficacy. A preferred polymer is polyvinyl pyrrolidone (PVP, and a preferred active is hydrogen peroxide.

The invention provides for a reactive surface that may be recharged or activated through any process that provides addition of the active to the surface, in the form of a liquid, gas or vapor. The amount of active applied may be varied to achieve different levels of surface activity to tailor the functionality to the desired task.

It is an object of the invention to provide a reactive composition comprising a hygroscopic polymer and an active, for incorporation into articles or application to hard surfaces, which provides biocidal and chemical decontamination/neutralization activity against a large variety of biological and chemical contaminants in a short period of time, including without limitation biological and chemical warfare agents.

It is another object of the invention to provide a reactive composition that has residual activity and maintains its biocidal and chemical decontamination/neutralization activity under organic load and dilution.

It is yet another object of the invention to provide a reactive composition that may be recharged or renewed with an active during use, without the need to remove, dispose of, and replace the reactive composition.

Still another object of the invention is to provide a reactive composition that is safe to handle and environmentally safe and that may be applied to porous and non-porous surfaces alike.

SUMMARY OF THE INVENTION

A novel reactive coating has been developed having biocidal and chemical neutralization/decontamination properties that are maintained, even under an organic load. The inventive coating is renewable or rechargeable by adding additional quantities of the active component to the coating after use or prolonged exposure to environmental contaminants, including biological and chemical warfare agents.

In one embodiment, the invention is directed to a reactive composition comprising a hygroscopic polymer and an active material mixed with or incorporated into the polymer. The active may be mixed with the polymer in a solution and dried to a film, or the polymer may be applied as a film and later charged with the active. The reactive composition may be applied to a surface or incorporated into an article during manufacture.

In another embodiment, the invention is directed to an article comprising the inventive compositions.

In a further embodiment, the invention is directed to a method for providing a reactive coating to a surface comprising the steps of applying a hygroscopic polymer to a surface of an object, drying the polymer to form a film, and then exposing the film to a charge of liquid or vaporized active agent.

In yet another embodiment, the invention is directed to a method for providing a reactive coating to a surface, wherein the active is combined with a polymer in solution and the polymer/active mixture is applied to a surface, followed by drying to a reactive film.

The biocidal and decontamination properties of the reactive coatings of the invention are renewable or rechargeable by exposing the surface or article to additional amounts of the active. There is no need to remove or discard the original reactive coating surface.

BRIEF DESCRIPTION OF THE DRAWINGS

FIG. 12 reflects inactivation (log reduction) of *B. anthracis* (Ames strain) spores by contact with 1300 K PVP crosslinked and exposed to VHP, using non-exposed PVP film as a control.

FIG. 16 reflects inactivation (log reduction) of *B. anthracis* (Ames strain) spores by PVP crosslinked onto a fabric wipe and CARC substrates exposed to VHP.

FIG. 18 reflects composite images of gram-stained and non-stained LDPE/PVP 80/20 masterblend film.

DETAILED DESCRIPTION OF THE INVENTION

Figure 1:
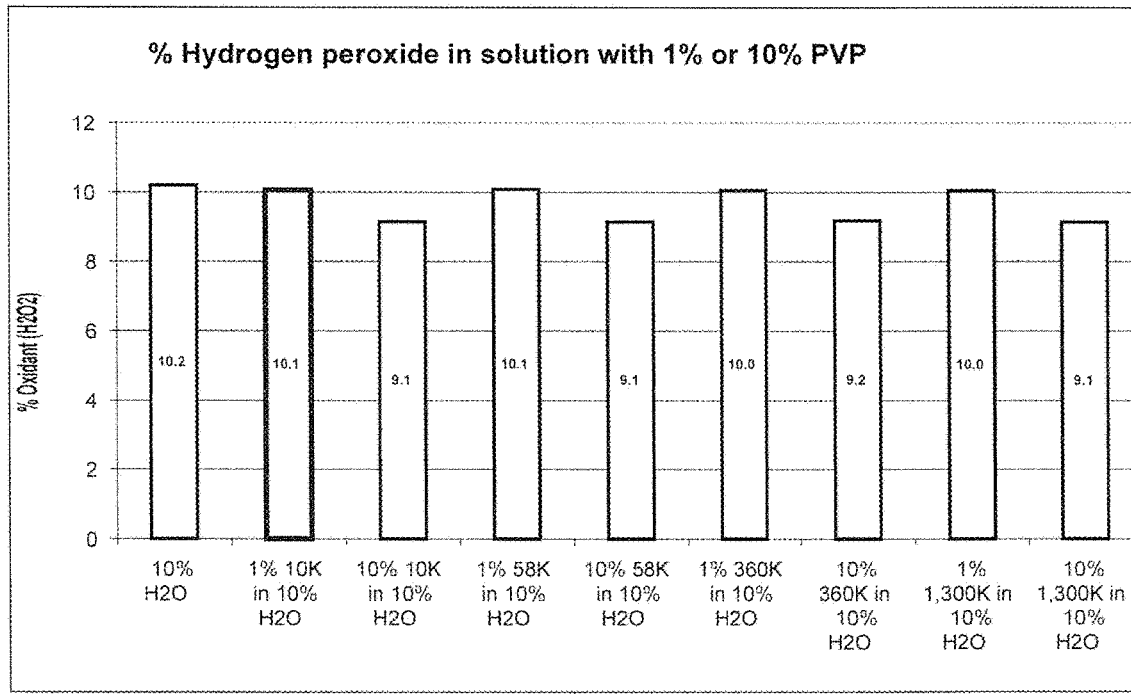
FIG. 1 reflects the percent oxidant achieved in solution when a 10% $H_2I_2$ solution is mixed with 1% or 10% PVP having various molecular weights (10-1300 K).

The invention is directed to a renewable or rechargeable reactive surface coating having biocidal (including sporicidal properties) and chemical neutralization or decontamination properties and methods for preparing and applying such a coating and applications for same.

For purposes of the invention, the following terms are defined:

"Active" means a chemical substance or other material having the capability of destroying living organisms or neutralizing or contaminating chemical or biological contaminants.

"Biocidal" means capable of destroying living organisms.

"Bactericidal" means capable of destroying living bacteria.

"Chemical neutralization" or "chemical decontamination" means rendering a chemical contaminant neutral and harmless to human or animal subjects.

"Germicide" means an agent that kills germs, especially pathogenic microbes.

"Hygroscopic polymer" means a polymer that is capable of absorbing water molecules or moisture from the environment.

"Microbe" means a living microscopic organism, such as a bacteria, protozoa, fungi, or virus.

"Microbicidal" or "microcidal" means capable of destroying living microbes.

"Warfare Agent" means a substance, chemical or biological, the toxic or disease-causing properties of which are used as a weapon.

For purposes of this invention, "biocidal", "microbicidal", "microcidal", "germicidal" and "bactericidal" are used interchangeably.

For purposes of this invention, chemical "decontamination" and neutralization are used interchangeably.

For purposes of this invention, "renewable" or "rechargeable" are used interchangeably.

For purposes of this invention, large molecular weights are expressed as abbreviations of the kilo Dalton (KDa) weight and are designated as "K" where applicable.

The reactive inventive compositions of the invention comprise a hygroscopic polymer combined with an active.

Polymers.

Hygroscopic polymers useful in the invention include, by way of example but are not limited to, polyvinylpyrrolidone (PVP), polyvinyl alcohol and mixtures thereof. Additional useful hygroscopic polymers include low density polyethylene (LDPE) and polyethylene glycol (PEG). Other polymers that achieve the desired biocidal and chemical decontamination properties also fall within the scope of the invention and would be known to one skilled in the art.

The invention is described primarily in terms of PVP, because it has already been successfully combined with liquid hydrogen peroxide to create commercially viable products, such as teeth whitening strips. It has in the past also been used as a blood plasma extender demonstrating its safety. PVP can exist in both liquid and solid form depending on how it is processed, leading to a variety of application options. It is for these reasons that it is a preferred polymer.

PVP exists and is available in a wide variety of molecular weights. Useful PVP polymers range in molecular weight from about 10 K to about 1300 K.

Low density polyethylene (LDPE) is also a hygroscopic polymer useful in the present invention. Useful LDPE polymers range in molecular weight (chain length) from about 1000 to about 130,000.

Hygroscopic polymers useful in the invention may be used individually or in blends with other polymers. For example, a blend of PVP and LDPE is useful and falls within the scope of the invention. Typically, the hygroscopic polymer associates with the active, while other polymers, even non-hygroscopic polymers, may be utilized in a blend to achieve various characteristics, provided that they do not limit the biocidal or chemical decontamination properties of the active.

While not wishing to be bound by theory, it is proposed that the unexpected results achieved by the inventive combinations may be due to a synergistic effect of the polymer(s) with the actives. The effect may be due to polymer weight and/or concentration or active concentration, or both.

Actives.

Actives useful in the present invention include without limitation peroxides, such as hydrogen peroxide liquid, vaporized hydrogen peroxide (VHP) or solid peroxide sources such as percarbonates and perborates; chlorine gas; peracetic acid; iodine; or mixtures thereof. Other useful actives include Chloramine-T (tosylchloramide or N-chloro tosylamide, sodium salt, an N-chlorinated and N-deprotonated sulfonamide used as a biocide and a mild disinfectant); and DCICA (dichloroisocyanuric acid) and its salts. Some of these actives may also be used as additive agents to a peroxide-based reactive composition.

Peroxide as an activator for a reactive surface has practical advantages. Peroxide is a worldwide commodity so local availability is assured in most regions. Peroxide at concentrations below 8% can be shipped via ground, water and air without restrictions. Peroxide is a common component in many decontaminants under consideration by the Department of Defense at this time. Technology currently exists to deliver peroxide in vaporous and liquid forms. As such, a focus of the invention is on the use of peroxide as an active, although the invention is not limited as such.

Hydrogen peroxide is a particularly preferred active as it is easily combined with a variety of polymers. It is also known as an antimicrobial and decontaminant. In addition, the inert breakdown products of hydrogen peroxide are water and oxygen, thus eliminating any long term toxicity hazards. Calcium and magnesium peroxides may also be useful peroxide sources as they have good long term stability in terms of total oxidant, although they are less preferred if film quality is an issue due to the large solid volume required. They may also take longer than a hydrogen peroxide solution to provide biocidal or decontamination effects.

The total amount of polymer (whether a single hygroscopic polymer, hygroscopic polymer blends or a hygroscopic polymer(s) combined with a non-hygroscopic polymer(s)) present in the inventive composition may vary and ranges from about 1 up to about 99 wt. %, based upon the total weight of the reactive composition.

The amount of hydrogen peroxide or other actives present in the inventive composition(s) may vary and ranges from about 1 to about 10 wt. %, but may range as high as 90 wt. %, depending on the form of peroxide used, i.e., applied as a solution or, if in solid form, in a dried surface.

While the inventive compositions are quite useful with the peroxide actives, optionally, other active additives may be included in the inventive compositions in amounts of at least about 1 wt. %, based upon the total weight of the composition. Useful active additives include Chloramine-T, DCICA, peracetic acid (PAA), chlorine, sodium carbonate, and solid peroxides, such as calcium and magnesium peroxide and sodium percarbonate or perborate.

The compositions of the invention may include other additives to affect processing, and/or performance or physical properties of the composition or resulting film. By way of example, additives that may be incorporated include, but are not limited to glycol or PEG's (polyethylene glycols) to make the surface more flexible, and vinyl acetate to decrease solubility and increase strength. Other useful additives will be apparent to one skilled in the art.

The reactive compositions of the invention may be prepared and/or rendered "active" in one of two ways. One approach is to incorporate both the active and the hygroscopic polymer into a solution by simple mixing and applying the mixture to a substrate, object or surface. Another approach is a two-step process in which the hygroscopic polymer is integrated into a substrate or onto a surface and the active is then applied through a liquid or vaporous application. Slightly better results have been obtained with the latter approach as it effectively concentrates the active at the surface allowing for better interactions with contaminants. It also permits the user to tailor the amount of active available on the surface for the particular application.

The inventive compositions may be applied to surfaces or incorporated into substrates in a number of ways. Application could be, by way of example, but not limited to, mixing the inventive compositions with a polymer blend prior to manufacture of a substrate or object, application to a surface using a brush, roller, spray, or any way that coating materials are applied, infusion or absorption onto/into fabric substrates and the like.

The inventive compositions offer significant advantages over traditional antibacterial coatings. In particular, the inventive compositions provide improved performance over traditional technologies, by combining components synergistically to provide efficacy over and above that available from a single component alone. The invention provides broad spectrum biocidal activity, including but not limited to bactericidal, virucidal and sporicidal efficacy. The inventive compositions also provide an opportunity for neutralization of chemical agents or toxins, without creating additional hazards. The inventive compositions are particularly for applications where chemical and biological warfare agents may be encountered.

Significantly, the reactive compositions of the invention perform well under organic load. Testing indicates that the efficacy of the surface is unaffected by certain organic loads.

The inventive compositions may be activated once, used, and then disposed of after their useful life. However, a significant and unique advantage is that the originally applied coating does not need to be removed, disposed of, or replaced after a "useful" life. The inventive compositions can be renewed or recharged when needed, or at regular intervals, to ensure their efficacy and continued use. Further, the concentration of the active at the surface can be controlled during the renewal process, providing the opportunity to tailor the surface to respond to different challenges or to modify the time between renewal or recharging of the active.

Because the surface formed by the inventive compositions is hygroscopic, the reactive surfaces formed by the inventive compositions draw organisms into the surface for greater contact and, hence, greater efficacy. However, depending on the polymer selected for use, the surface does not have to be hygroscopic, although hygroscopic polymers are preferred.

The inventive compositions function to enhance proven decontamination processes and address many of the shortcomings of current decontamination procedures such as:

Cleaning operator variability

Efficacy on all difficult-to-reach surfaces

Long lasting efficacy—protection stays in place after cleaning/decontamination process Chemistry is safe to use and environmentally friendly Physical Property Modifications.

A variety of physical properties of the inventive reactive surface coatings may be optimized for use in a number of different applications. Properties such as solubility, quality, flexibility, and adherence to substrates determine the usefulness of the inventive compositions in any particular application. A smooth surface and even distribution of components across the surface is an important film quality property that should be considered.

Surface properties may be affected by the method of preparing the surface, including but not limited to casting, coating and extruding. In addition, layering or sandwiching techniques using multiple layers of different polymer types, may be used to achieve the desired properties, as one skilled in the art would understand.

Other approaches used to affect surface quality included preparing components in a solvent solution, such as methanol, to improve surface wetting properties. Varying the concentrations of each polymer needed to coat a surface is also important to assure that a usable film or coating is achieved. For example, if too little PVP is used, a powdery residue would cover the surfaces, but no film would be created. Likewise, with polymer blends, such as PVP/LDPE, limitations on the PVP concentration were set based on the amount of holes or tearing that occurred during processing.

Blends of PVP/LDPE can be adjusted to impact the quality of the film created. Varying the level of each component of the blend can affect the surface texture of the film, the thickness and other characteristics that define the quality of the film.

Solubility may play a role in two ways depending on the final use application. PVP has a high affinity for water and is highly soluble in most solvents. This high solubility makes it ideal if the reactive coatings are used in removable applications, such as an application where a clear removable coating is needed that contains decontamination properties. Non-limiting examples of such an application include windshields, lights, or interior surfaces that are washed more frequently. Solubility plays an important role in tailoring reactive compositions for short term use.

PVP may also be cross-linked into a water insoluble film through a UV or chemical process. Cross-linked PVP retains all of the properties of PVP without being soluble. A non-water-soluble version of the inventive compositions allows for use in many applications. Cross-linked PVP swells upon exposure to water. This may present some tactile and visual inconsistencies when compared to other polymer complexes that retain their properties regardless of liquid exposure. Yet, this absorptive property can be utilized to capture chemical warfare agents and indicate areas where exposure has occurred. The change in surface property can also be used to highlight areas for decontamination and reduce the decontamination procedures from a whole surface to a designated area.

Incorporating PVP into other polymer substances, while still retaining its desired properties, is a way to limit the solubility of PVP. Co-extrusion of PVP with LDPE is an example of such an approach. Another simple approach would be to add PVP to other commercialized coatings. As long as the PVP is accessible for activation by a liquid or vaporous active, this approach is feasible. Applications for non-water soluble versions include, but are not limited to, tent liners and high touch areas where self-decontamination would be essential.

Flexibility is one property that plays an important role in the usability of the coatings. Reactive compositions of the invention may be used with pliable surfaces, such as fabric, and on hard surfaces. If films are brittle, they may crack, which creates an uneven surface or an inadequate surface for use. Film flexibility may be optimized by using known additives, such as glycerin, to reduce brittleness.

Adhesion and incorporation to a substrate is an important property. The inventive compositions may be applied to already coated surfaces without peeling or cracking of the base coating. In many applications, it is desirable to have a film that cannot be easily removed by scrubbing. The inventive compositions have been shown to be effective when applied to a large variety of substrates and surfaces.

Use/Applications.

The invention lends itself to incorporation onto a surface as a permanent renewable/rechargeable long term coating or into a single use device for shorter term protection, such as a uniform, gown, sheet or other fabric, stick on pads for application to high touch critical surfaces, and the like. The invention is effective when applied to porous and nonporous surfaces. Accordingly, the inventive compositions may be incorporated into a wide variety of substrates to create durable reactive materials or can be applied to a wide variety of existing surfaces.

A wide range of uses are demonstrated for the inventive compositions in addition to the military applications discussed herein. These range from applying the reactive compositions to already coated substrates, fabrics, objects and hard surfaces, to the formation of plastic films and sheets for use as reactive surfaces. A safe and effective reactive surface would find applications in products/markets, such as healthcare, for durable surfaces, walls, floors, hardware, knobs and handles, push bars, bed rails, covers for high touch surfaces, and disposable items. The inventive reactive coatings may also be used as a part of a filtration system to remove and neutralize chemical or biological contaminants from an air stream. Consumer products such as personal care items, toys, kitchen surfaces, public high touch areas, knobs, push plates, handles and packaging materials are also viable applications.

Other applications will be evident to one skilled in the art, based upon the quality of film, solubility, flexibility and adherence to substrates of many varieties that were noted and achieved in the evaluation of the inventive compositions.

The invention is further described by the examples set forth herein.

METHODOLOGY USED IN EXAMPLES

Because evaluation of reactive surfaces is a developing field and standardized test methods are not yet available, it was necessary to identify and assess test methods currently in use and to develop application specific methods where necessary. The methods utilized are described generally below. To the extent that any particular example used different methodology, it is described within the example.

Active Ingredient.

The amount of the active ingredient in combination with the polymer was evaluated prior to any efficacy testing. Since oxidative chemistries were selected for the development of the technology, the majority of evaluations were performed using a sodium thiosulfate titration in combination with potassium iodate as a preferred method. This technique was used to measure the amount of active in solutions when evaluating candidate technologies as well as evaluating the concentration of actives on surfaces. Modifications were adapted for testing solid samples.

Physical Properties Assessment.

Physical properties were assessed using both qualitative observations and quantitative methods as appropriate. In some cases, simple observations were deemed adequate to differentiate between potential components in the areas of surface finish, flexibility, and porosity. Microscopy was used to assess where a particulate was located in a substrate and how evenly it was distributed. IR Spectroscopy was used to identify hydrogen peroxide positively as the oxidant present at the surface of the inventive coatings. Testing was also performed using Near IR in conjunction with grazing angle to try and elucidate the level of hydrogen peroxide penetration into the coatings. Nitrogen testing was used to verify the composition of PVP in film blends. Samples were excised from various places in any given film sample and tested to determine if there was a consistent amount of the intended PVP concentration.

Chemical Efficacy Test Methods.

Chemical efficacy testing was completed using chemical agent simulants.

Chemical agents useful as simulants include:

CEPS (2-chloroethyl phenyl sulfide), DBS (Dibutyl sulfide) and Thioanisole for HD (nitrogen mustard)

DEMPT (Diethyl methyl phosphonothioate) for VX (a man-made chemical agent known as a nerve agent and considered one of the most toxic chemical warfare agents)

Use of simulants to predict the outcome for real agent testing is well-known and several correlation models have been developed that assist with predicting the outcome of real agent testing. While no simulant is 100% predictive of the results of live agent testing, the results served to differentiate between promising technologies and those that did not provide value.

Three general types of tests are used to assess chemical efficacy: solution testing with simulants, surface testing with simulants and high resolution Magic Angle Spinning Nuclear Magnetic Resonance (HRMAS NMR) with live agents.

Because solid-solid reactions are slow, polymers and actives were tested in solution at low concentrations. These liquid models allowed for the separation of promising decontamination candidates before considerable time and process development was spent on testing relevant surfaces. Chemical simulant testing was performed on reactive surfaces having surface areas of approximately 1 cm$^2$. The reactive surface was placed in a 10 mL glass vial and spotted with 1 μL of a chemical warfare agent as listed above. The system was allowed to react for the time allotted for the particular simulant. Reaction times were based on previously established correlations between simulants and live agents and depended on the target agent. After the reaction period, the surfaces were extracted in iso-octane. A fixed volume of iso-octane was then transferred into a vial containing a quench solution to stop all interactions. Analysis was performed on a gas chromatograph couple with a mass spectrometer (GCMS) to assess the concentration of warfare simulant extracted from the reactive surface. External standards were prepared at 100%, 50% and 25% reactive concentrations. All results were reported as percent reduction of the original agent/simulant.

HRMAS NMR.

Live agent testing was conducted on a cloth substrate to which the polymers of the invention were applied. The cloth samples were then placed in a VHP chamber and exposed to 400 ppm VHP for 30 minutes for activation. Unless otherwise noted in the examples, all VHP activation occurred at 400 ppm for 30 minutes.

Treated film samples were tested to ensure appropriate activation had been achieved. For an exposure of 1 g/m$^2$ or 0.1 mg/cm$^2$, a square of 1 cm$^2$ area was cut from the substrate within 6 hours of VHP activation. Untreated (non-VHP) samples were also analyzed to serve as a test control. The square was then rolled into a cylinder and placed into a HRMAS rotor (sample container). A 1% dilute solution of the agent was prepared in iso-octane (2,2,5 trimethylpentane) by weight. Using the weight to volume concentration a volume equivalent to 0.1 mg of the agent was pipetted onto the film sample. An effort was made to distribute the solvent as evenly as possible over the surface of the film. The solvent was allowed to evaporate for 5 minutes, but some was still observed in the NMR spectrum. The samples were analyzed periodically by NMR until 24 hours after spiking. For HD, $^{13}$C was monitored, for VX and GD (soman, a nerve agent), $^{31}$P was monitored.

Microbiological Efficacy Test Methods.

Microbiological testing was completed using accepted *B. anthracis* surrogates. Microbiological efficacy testing was performed using protocol derived from ASTM standard designation E 2197-02: standard quantitative disk carrier test method for determining the bactericidal, virucidal, fungicidal, mycobactericidal and sporicidal activities of liquid chemical germicides.

*B. subtilis* ATCC 19659 spores were chosen as a surrogate for *B. anthracis* spores as supported by the literature and previous correlation studies that demonstrated that *B. subtilis* spores are more difficult to inactivate than *B. anthracis* spores. In our efficacy testing, a challenge of 10$^5$ CFU was targeted and delivered to a circular area on the test substrate roughly one-third of a centimeter in diameter or 0.085 cm$^2$. This is equivalent to an excess of 10$^{10}$ CFU m$^2$, in excess of the starting challenge of 10$^8$ CFU/m$^2$ objective level set for JSSED/JPID (Joint Service Sensitive Equipment Decontamination/Joint Platform Interior Decontamination) systems. Other challenges were also utilized.

To challenge potential reactive coatings, a portion of the candidate material was inoculated with a suspension of *B. subtilis* ATCC 19659 spores. After inoculation, the liquid inoculum and material were incubated, allowed the coating to inactive the spore challenge. Once a set incubation time passed, the reaction was quenched by chemical and physical action of flooding the coupon sample and reactive coating material with neutralizing growth medium.

Once quenched, the reaction mixture, consisting of the reactive coating, spore challenge and neutralizing growth medium was subjected to treatment in an ultrasonic cleaning water bath to facilitate release of the spore challenge from the reactive coating materials into the neutralizing growth media. After sonication, the growth media was assessed for surviving spores via standard microbiological procedures, i.e., dilution of the growth medium and enumerating colony forming units (CFU's).

The resultant CFU dilution data were used to estimate the LOG$_{10}$ spore density on the material at the time the reaction was quenched. In assessing a single material, several sequential incubation times were tested, to allow an analysis of the LOG$_{10}$ spore density as a function of time. The rate at which the candidate coating inactivated the spore challenge, inferred from the drop in LOG$_{10}$ spore density was used to compare the efficacy of various candidate materials.

Reactive coating materials were assessed for their ability to inactivate *B. anthracis* (Sterne) and *B. anthracis* (Ames) spore challenges in a manner similar to that described for assessing inactivation of the surrogate challenge, *B. subtilis* ATCC 19659 spores, above. Minor modifications were made to the protocol to the extent necessary to comply with safety procedures required for live biological agents.

Activation Methods/Incorporation of Active.

Coating materials were activated using one of three methods: VHP activation/exposure of the polymer surface, active incorporation directly into the polymer prior to drying or liquid applications of the active to a dried polymer surface. The typical exposure cycle for samples was 30 minutes at 400 ppm hydrogen peroxide in a vaporous hydrogen peroxide (VHP) chamber. Hydrogen peroxide application in liquid form was also tested with pre-cast film. Pre-cast film samples were prepared and cut to the desired size and then exposed to solutions of liquid hydrogen peroxide at concentrations of 1-7% for various time periods. The samples were allowed to air dry and tested for percent oxidant, i.e., hydrogen peroxide. Other samples were prepared by adding liquid hydrogen peroxide or other active to PVP first, followed by casting.

Sample Preparation.

PVP can be incorporated into films in a wide variety of ways to tailor its performance. This flexibility made it possible to explore a range of applications. Through the use of various additives and manufacturing methods, a wide variety of films were produced for testing.

Various film production methods were utilized to achieve certain desired properties. Each of the techniques addressed a particular application for the inventive technology and provided a specific benefit in creating a reactive surface.

Casting.

The simplest form of film production was casting. This basic approach produced films by adding a fixed volume of the polymer solution to a surface with a known area. Small weight boats, GC vial caps, glass vials, and CARC panels were all used as surface templates. The film produced tended to be very uniform, creating excellent surfaces for testing. The casting method also allowed for the preparation of a large number of samples very quickly. A similar technique used a Meyer bar to control the thickness of the films created on large sheets of glass and Viton.

Preparations of the PVP-HP technology in water tended to have a high surface tension, which would cause beading rather than spreading on a surface when attempting to produce films. Methanol was added to the solutions to reduce the surface tension for film production, which was key to creating a uniform thickness in films and reducing drying time.

Given that solid-solid interactions are much slower than liquid-liquid reactions, an effort was made to create a surface with the maximum area for "active" incorporation to increase reactivity. One method available for creating high surface area polymers is electro-spinning. Samples of nano-spun PVP were made and collected on a nylon web backing, which allowed for the fibers to be manipulated without collapsing their structure. Problems arose due to the high water-solubility of PVP, which made it very sensitive to moisture in this form and thus unable to retain properties during active application testing. Even so, this technique is deemed to be viable when used in combination with other polymers or additives or crosslinking to provide the desired structure and properties of the polymer for active incorporation.

Crosslinking to a Surface.

PVP is a very soluble polymer, not only in water but in a wide variety of solvents. Not all applications benefit from a soluble system. Two approaches were investigated for reducing the solubility of the PVP. One technique was to cross-link the polymer, creating an insoluble form on a given surface. Cross-linking is a process whereby polymer chains are chemically linked to form a polymer network. PVP can be cross-linked to make a non-soluble surface in a variety of ways known to one skilled in the art, including without limitation exposure to a specific wavelength of UV light or through the use of chemical cross-linkers, i.e., initiators. The use of chemical cross-linkers would have required evaluation of multiple chemicals and added another variable to the testing. As such, a UV light tunnel was used to cross-link PVP, which can be easily scaled up for production.

The UV chamber was equipped with four 24 watt rated UV bulbs, each 30 cm long. The lamps were at a height of 5 cm above the surface of the samples. These lamps emitted UV A, B, C, and V rays with the particular range of interest for cross-linking of 250-260 nm (UVC). Light intensity measurements were taken before each batch exposure ranging from 114-190 mJ/min. Optimum polymer conditions for cross-linking were determined to be 10% w/w of 360 K PVP with a 2 hour UV exposure time with the UV conditions given above. A catalytic amount of hydrogen peroxide (20 mM) was added to initiate the reaction. The method reproducibly generated films with >95% of the surface cross-linked.

Percent crosslinking of samples was determined on a weight basis. The percent cross-linking (or percent gel) was a comparison of the amount of insoluble (cross-linked) PVP to the weight of PVP added to the surface. After UV exposure, some samples were placed in beakers with 100 mL deionized (DI) water and allowed to soak 24-72 hours. This allowed the uncrosslinked PVP to go into solution while the crosslinked portion remained in contact. The remaining crosslinked polymer was then captured by filtration and dried at 50° C. overnight. The weight of the non-water-soluble polymer was measured. Percent cross-linked (% gel)=weight of the non-soluble polymer/weight of the polymer applied×100%.

Substrate Integration.

Another way of reducing solubility of PVP was to integrate it into a substrate that protected it from surface water while at the same time making it available to absorb peroxide and provide surface efficacy. The combination of PVP with low density polyethylene (LDPE), creating a substrate by extrusion, was tested. The object was to create a matrix of the two materials that would provide a balance of usability and durability and provide water, while at the same time making it available to absorb peroxide and provide surface efficacy.

Extrusion.

Extrusion is a well-established process for converting plastics into usable materials. Several different extrusion methods were tested. PVP has a degradation temperature below that of its melting point. This means that PVP is not suitable for extrusion by itself so that it must be combined with a polymer that will provide the desired properties. LDPE was chosen to combine with PVP because of its availability, excellent extrusion properties at a temperature below the degradation temperature of PVP and its well defined polymer characteristics.

Extrusion of the samples was done in a bench top extruder where all the materials were mixed together, then placed into a twin screw extruder. The materials were then allowed to recirculate for a time, then extruded into a 1 inch wide film. Larger samples were produced using a pilot lab scale machine capable of producing 4 inch wide films. PVP and LDPE were introduced into the machines in two ways. One method was to pre-blend the dry ingredients and feed the mixture into the extruder. This produced variable results due to size separation of the LDPE and PVP in the feed hopper. Another method was to create a "master blend" prior to feeding into the extruder. The master blend was made by mixing the PVP and LDPE in a separate extruder that encouraged mixing. This forced the creation of a pelletized material that had a consistent composition. Testing of the master blend pellets prior to extrusion confirmed that the master blend process was effective at evenly distributing the PVP in the LDPE.

An evaluation of three molecular weights of PVP, i.e., 58 K, 360 K and 1300 K, showed that the 1300 K had the most even distribution in the substrate. (For purposes of these examples, large molecular weights are expressed as abbreviations of the kilo Dalton (KDa) weight and are designated as "K".) Additionally, the amount of PVP that could be incorporated was also evaluated at 10, 20, 30 and 40%. The 40% incorporation was used for the production of the master blend, but was not suitable for extrusion alone as there was significant tearing. The 30% PVP blend provided less than ideal surface conditions.

In some examples, polyethylene glycol (PEG) was added to the LDPE/PVP blend to improve its physical properties, notably flexibility. PEG is a non-toxic, water soluble polymer similar to PVP. It also has a lower melting point, similar to that of LDPE, and without the degradation experienced with PVP. Incorporation of PEG was intended to improve the smoothness and elasticity of the films while lowering the melting point of the system in order to minimize degradation of PVP. Due to the solubility of PEG and PVP in water, concentration of PEG was limited to about 2%.

Effect of Polymer Weight

Finally, some physical properties of the technology can be modified through the selection of the polymer molecular weight. For the purposes of the invention, four average molecular weights of PVP were evaluated. The average molecular weights screened were 10 K, 58 K, 360 K and 1300 K. No single average molecular weight always performed best. Different molecular weights proved optimum for various applications. Films using lower molecular weight polymer created matte surfaces that were easily solubilized. Higher molecular weights were more suitable for cross-linking by UV light.

Comparative Example A

Commercial-off-the-shelf (COTS) products that claimed to generate hydrogen peroxide on surfaces were tested for efficacy and may be compared to the inventive compositions.

Three different COTS paints were identified that claimed to create peroxide on surfaces in the presence of water and ultraviolet (UV) light. The products tested were from e-Paint® and included E-Paint® SN-1, E-Paint® ZO (both of which are solvent based) and E-Paint®-2000 (water-based). These products were designed for application to ship bottoms to prevent fouling by biological organisms.

Products were applied to coupons as specified by the manufacturer and tested under recommended conditions. Surfaces coated with the three paints were evaluated for concentration of hydrogen peroxide generated over a specific time period. This was followed by efficacy testing against a biological agent surrogate and a chemical agent simulant. Testing was also completed using different levels of surface moisture and exposure to UV light in an attempt to maximize hydrogen peroxide content.

While the products may be functional for their intended purposes, no conditions or methods were identified that demonstrated that these particular products provide the level of reactivity needed for use as a chemical or biological agent surface decontaminant. Test results consistently indicated that the level of surface oxidant generated by these COTS products was too low to be of any value as a reactive surface. A critical consideration is that these products are intended to work very slowly and consistently over a long period of time in use. Hence, while it is possible that they may show some efficacy over extended times, they did not meet the desired reaction time requirements for immediate efficacy.

When applied to coupons using two coats to achieve the manufacturer's recommended thickness and placed in 10 mL of DI (deionized) water and positioned for exposure to UV light or no UV light for 72 hours, aliquots of the water solution were titrated to determine the level of hydrogen peroxide. The results showed only minimal hydrogen peroxide production (<0.0013) with only a slightly higher result when using UV light.

The HD simulant dibutyl sulfide (DBS) was used to test efficacy for decontamination, despite the low levels of peroxide assessed. Two coats of paint were applied to wooden tongue depressors to meet the manufacturer's recommended thickness. Coupons of each paint were then spotted with 1.5 µL of a solution of 50% DBS and 5% dodecane in isopropyl alcohol and water (at 0% and 2.5%). Samples were tested using UV light or no UV light. The solution was allowed to react with the surface for 10 minutes before the sample was transferred to a test tube containing 10 mL of isopropyl alcohol for extraction of the DBS and related compounds. At 15 minutes (five minutes of extraction), a sample of the extraction solution was transferred to a vial and analyzed by GCMS using the appropriate method.

The two solvent-based paints appeared to provide better efficacy than the water-based paint in terms of percent decontamination; however, there was no way to differentiate between the absorption of the DBS into the surface and a reaction. The results appeared to be an indication that the simulant was absorbed and held by the paint surface. In theory, no hydrogen peroxide could be generated in a system without the presence of water. Yet, there was no differentiation between the efficacy of the samples with water and without water, and it was thus concluded that there was little if any value from the generation of the hydrogen peroxide.

Previous correlations between the simulant DBS and HD indicate that if 100% decontamination of DBS is not achieved, as in the case of this example, then no more than 50% HD would be decontaminated. Hence, the results of this test indicated that even with water and UV light, the systems did not provide either the level of surface peroxide required for efficacy or any meaningful neutralization of the HD simulant DBS.

A microbiological study was done on the two of the materials (2000 and SN-1) for completeness and to determine if the products might function in this area. A series of time bactericidal efficacy studies were performed using a *S. aureus* ATCC 6538 challenge.

Neither of the paints demonstrated any discernible LOG reduction of cells in the suspension in the time frames used (30, 60 and 90 minutes). Both paints were observed as sequestering the peroxide that they generated. It must be noted that bactericidal activity may be to a large extent dependent on the kinetics of interaction between the paint surface and the *S. aureus* cells and hence the assessment might be biased toward little or no activity. Even so, the results revealed that the paints did not have performance capabilities relative to that of the inventive compositions, namely, moderately rapid inactivation of a high titer biological challenge.

Comparative Example B

A dry blend of peroxide and PVP, commonly known as Peroxydone, was also evaluated. This material is most commonly found in a gel for use in products such as teeth whiteners.

Testing was performed to determine how Peroxydone compared to the inventive compositions. Two versions of Peroxydone, Peroxydone 30 and Peroxydone 90, which differ in molecular weight, were evaluated. When tested as a solution and compared to the inventive PVP-HP solutions, these commercial materials showed a much lower level of hydrogen peroxide than the samples of the inventive compositions. This lower peroxide concentration is likely the reason for the significantly lower bactericidal activity of the commercial Peroxydone solutions.

Peroxydone 30 and Peroxydone 90 were prepared as solutions at 5% and 10% (wt./wt.) and evaluated for hydrogen peroxide content by titration. A concentration of up to 2% hydrogen peroxide (by weight) was achieved. Live agent testing of HD with hydrogen peroxide solutions indicated that 5% is needed for this active to be effective alone. Due to viscosity concerns, Peroxydone concentrations could not be increased and thus limits the active concentration that could be achieved using this material.

Peroxydone 30 and Peroxydone 90 were assessed as liquid germicides (10 mL prepared in distilled water at concentrations of 1.0%, 5.0% and 10.0% wt./vol.) for staphylococcicidal efficacy by comparing the survival of a portion of liquid bacteria culture (*S. aureus* ATCC 6538) exposed to the liquid for a period of time with a portion of bacteria that has not been exposed to the liquid. The LOG difference between the two samples was used as a comparison metric.

The microbiological evaluation corroborated the chemical analysis. The aqueous Peroxydone solutions were not found to be bactericidal within the time frames tested (15, 30 and 60 minutes).

These comparative analyses of commercially available products demonstrated that despite their ability to generate hydrogen peroxide, the concentration of hydrogen peroxide was insufficient to achieve chemical decontamination efficacy or biocidal activity with the rapidity and completeness of the present inventive compositions.

Example 1—Oxidant Content and Efficacy of PVP/Hydrogen Peroxide in Solution

Many materials significantly degrade hydrogen peroxide (HP) when blended in solution. The first step, therefore, in determining whether PVP can be used with HP was to create blends of different concentrations and molecular weights of components and measure the impact on peroxide concentration.

Four molecular weights of PVP were tested at two concentrations, 1% and 10%. The molecular weights of the PVP were 10 K, 58 K, 360 K and 1300 K. The concentration of hydrogen peroxide used was 1%, 5% and 10%. The solutions were measured for total oxidant and results were analyzed for trends that would indicate that the hydrogen peroxide was degrading, rather than complexing with the PVP polymer. The resulting hydrogen peroxide concentrations are shown in FIG. 1 and in Table 1 below.

TABLE 1

| Effect of the addition of PVP to HP | | | | |
|---|---|---|---|---|
| Molecular Weight | Concentration | 1% $H_2O_2$ | 5% $H_2O_2$ | 10% $H_2O_2$ |
| Control | Water Only | 1.0% | 5.1% | 10.2% |
| 10K PVP | 1% PVP | 1.0% | 5.0% | 10.1% |
|  | 5% PVP | 1.0% | 4.8% | 9.7% |
|  | 10% PVP | 0.9% | 4.6% | 9.1% |
| 58K PVP | 1% PVP | 1.0% | 5.0% | 10.1% |
|  | 5% PVP | 1.0% | 4.8% | 9.7% |
|  | 10% PVP | 0.9% | 4.6% | 9.1% |
| 360K PVP | 1% PVP | 1.0% | 5.0% | 10.1% |
|  | 5% PVP | 1.0% | 4.8% | 9.7% |
|  | 10% PVP | 0.9% | 4.6% | 9.2% |

TABLE 1-continued

| Effect of the addition of PVP to HP | | | | |
|---|---|---|---|---|
| Molecular Weight | Concentration | 1% $H_2O_2$ | 5% $H_2O_2$ | 10% $H_2O_2$ |
| 1,300K PVP | 1% PVP | 1.0% | 5.0% | 10.0% |
|  | 5% PVP | 1.0% | 4.9% | 9.7% |
|  | 10% PVP | 0.9% | 4.6% | 9.1% |

The data shows that as liquid PVP of varying molecular weights was blended with liquid HP in varying concentrations, the impact on available oxidant was negligible. The ability to measure total oxidant was reduced by the same amount as the presence of PVP, i.e., 10% PVP caused a 10% reduction in measured oxidant concentration—indicating that little or no degradation of the active occurred (FIG. 1). This holds true for hydrogen peroxide concentrations from 1-10% over all four molecular weights of PVP tested. (See Table 1).

Biological Assessment Methods.

For this example, time kill studies were performed to evaluate the microbiological efficacy of various formulas. For solution embodiments, microbiological challenge tests were performed using *S. aureus* ATCC 6538. The organism suspension was diluted once to a $1 \times 10^8$ concentration in Butterfield's buffer. 100 µL's of the suspension was pipetted into 9.9 mL of each test formula and mixed. Samples of 100 µL's were removed from this solution at specified times and neutralized by adding 9.9 mL of LAT broth with 1% catalase. The tubes of neutralized organisms were then serially diluted and poured into plates. The plates were incubated at 37° C., or as required by the organism being tested. After 1 to 2 days of incubation, the plates were removed and counted recording results per internal Aerobic Plate Count Method (MCM 200.05).

Four molecular weights of PVP (described above) were tested at two concentrations, 1% and 10%. The hydrogen peroxide concentration was 10% in all four solutions and 10% hydrogen peroxide was used as a control. 10 mL of each solution shown in FIG. 2 were assessed for biocidal activity by challenging them with a buffer suspension culture of *S. aureus* ATCC 6538 transferred from solid media. The reaction was quenched at 15, 30 and 60 seconds with LAT broth (letheen broth supplemented with asolectin and tween (1% v/v catalase)) and subsequently assayed for CFU. Each solution/time point was tested three times. The resulting mean LOG reduction for each solution/time combination is set forth in FIG. 2.

Figure 2:
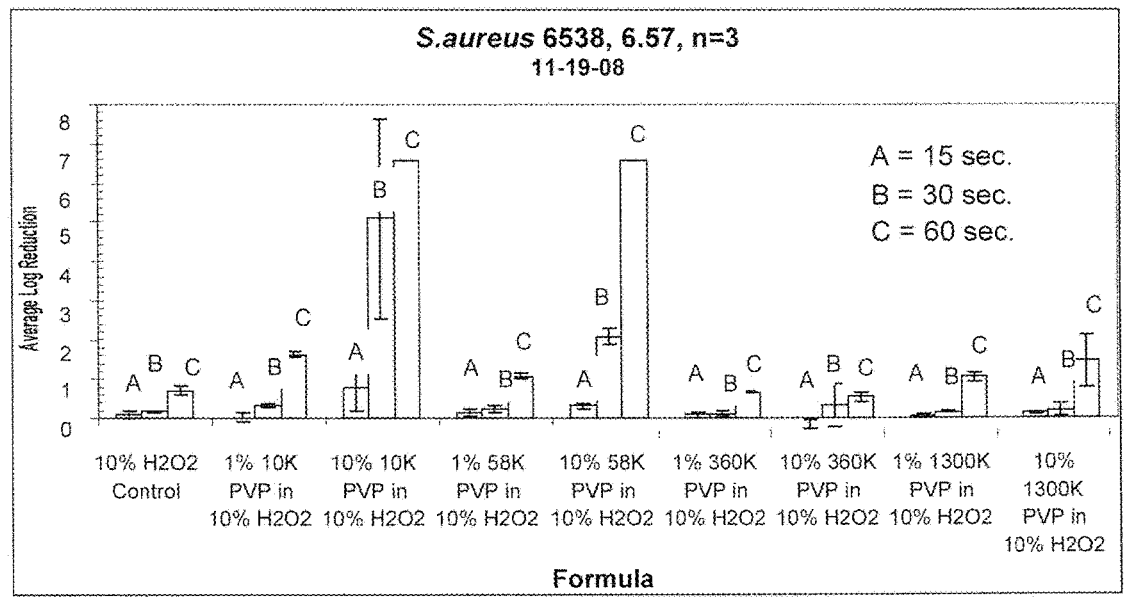
FIG. 2 reflects the average log reduction in a time kill study for the $H_2O_2$/PVP combination of FIG. 1 using *S. aureus* ATCC 6538.

Primarily, FIG. 2 data showed that solutions of PVP-HP are efficacious in inactivating a buffer suspension of *S. aureus* ATCC 6538 cells. The data also demonstrated the relationship between the efficacy of a PVP-HP solution and the molecular weight of the PVP in the solution. Where efficacy is indicated, as in 58 K and 360 K PVP solutions, there was also a relationship between efficacy and the percent inclusion of PVP in the solution. Increasing the PVP concentration increased the efficacy of the solution, and lower molecular weight PVP is more effective than higher molecular weight PVP. The data demonstrated that low molecular weight PVP's (10 K or 58 K) with 10% hydrogen peroxide outperformed 10% hydrogen peroxide or PVP solutions alone when tested against *S. aureus* in a time kill study. The effect was also proportional to the amount of PVP present in the solution. This means that 1% PVP with 10% hydrogen peroxide had a greater effect on *S. aureus* than 10% hydrogen peroxide alone, but 10% PVP with 10% hydrogen peroxide outperformed both solutions.

Understanding the impact of the PVP-HP complex on bactericidal efficacy allowed for the transition of testing of the decontaminant in solution to the formation of films and the production of a reactive surface.

Example 2—PVP and Hydrogen Peroxide Cast Films

Films were prepared (cast) from solutions of hydrogen peroxide (10% and 20%) and PVP, by letting 2 mL of each of the solutions dry in the bottom of 4 dram glass vials. A variety of molecular weights of PVP were used, including 10 K, 58 K, 360 K and 1300 K. Each concentration of hydrogen peroxide was used with each molecular weight of the PVP. Initial and final weights of the vials were used to calculate the oxidant concentration of each sample.

Figure 3:
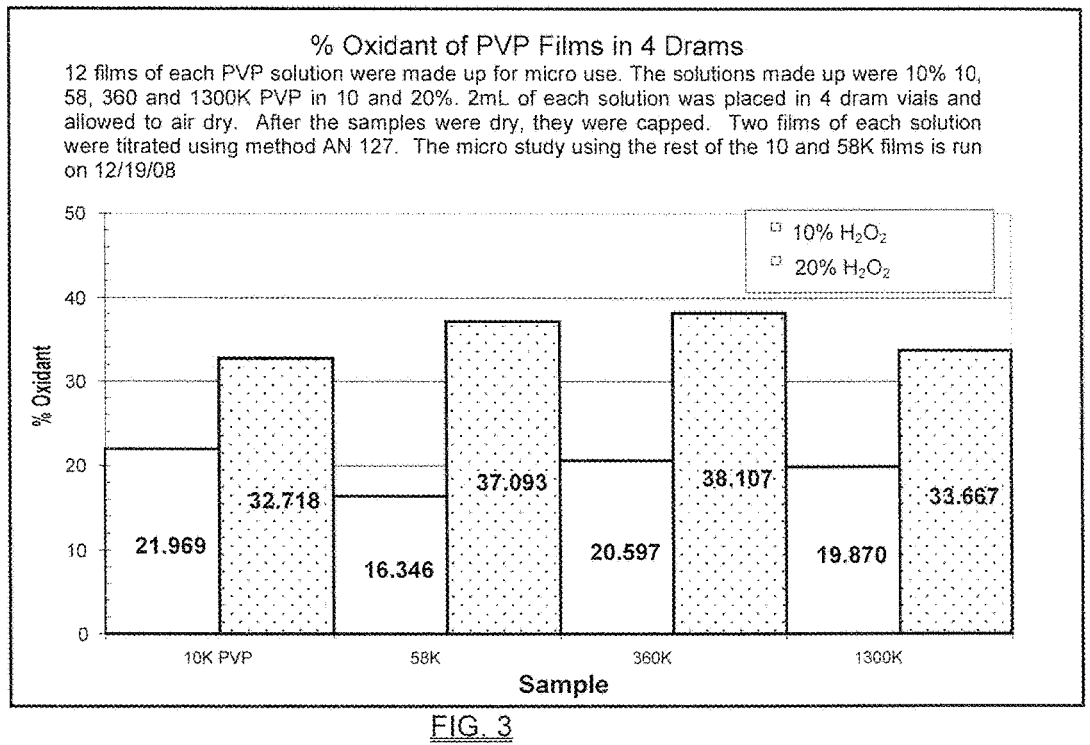
FIG. 3 reflects the percent oxidant achieved in a film when 10% and 20% $H_2O_2$ is mixed with 10% PVP (10K, 58 K, 360 K, and 1300 K) and allowed to air dry to a film.

The results are shown in FIG. 3. The hydrogen peroxide concentrations in the films increased as they dried. Hydrogen peroxide concentrations increased up to two times the concentration in solution. This example demonstrates that PVP films can be made with a very high level of inherent oxidation potential. The measured oxidant levels were about twice that of the initial concentration. There appeared to be no difference in oxidant potential based on the molecular weight of the PVP.

Microbiological Testing.

The microbiological testing procedure for used surfaces was modified QCT2. The organism to be tested was diluted to a $1 \times 10^7$ concentration in Butterfield's buffer. 20 µLs of the inoculum (*S. aureus* ATCC 6538) was then applied to each test surface at time zero ($t_0$). The surfaces may include inverted GC vial caps, glass vials, cloth, painted surfaces using a chemical agent resistant coating (CARC), commonly used on military equipment, or any other surface with the invention applied to it. The surface used for this example was a film created at the bottom of 4 dram vials. After the appropriate contact time, the surface was neutralized by adding 10 mL of LAT broth with 1% catalase, or a volume appropriate to cover the test surface. The surfaces with the neutralizer were vortexed briefly, sonicated for five minutes, vortexed briefly again, and sampled. Serial dilutions were pour-plated with organism appropriate agar. The plates were incubated at 37° C., or as required by the organism being tested. After the required incubation period (organism specific), the plates were counted and recorded per internal Aerobic Plate Count Method (MCM 200.05).

Figure 4:
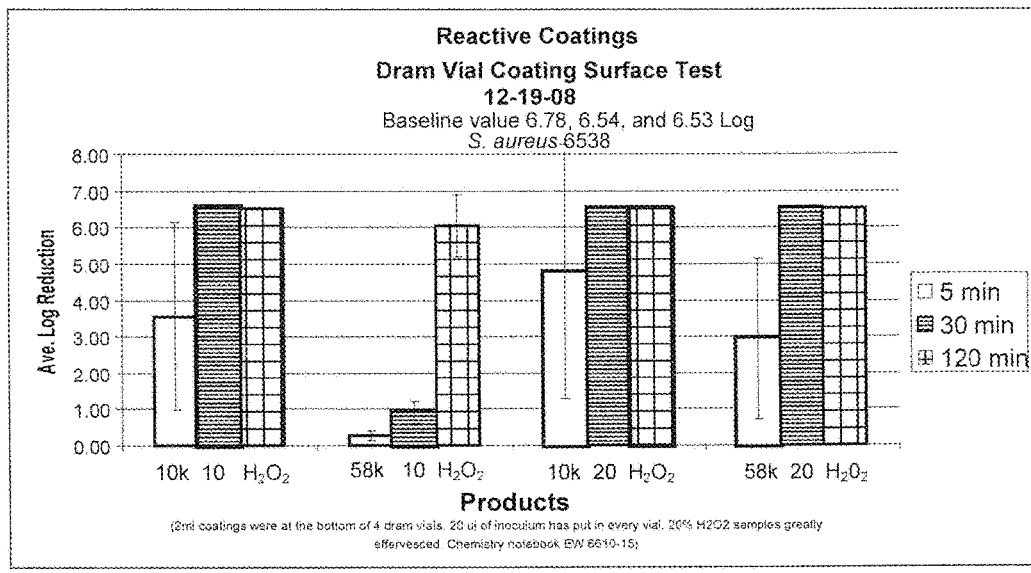
FIG. 4 reflects the average log reduction of reactive coatings of the invention inoculated with *S. aureus* ATCC 6538.

The results are shown in FIG. 4 for average LOG reduction at 5, 30 and 120 minutes for 10 K and 58 K PVP films made with 10% $H_2O_2$ and 20% $H_2O_2$ solutions. The microbiological study on the Example 2 films showed that the molecular weight of the PVP, as well as the hydrogen peroxide concentration, had an impact on the microbiological testing. For these samples, a six log reduction (complete kill) of *S. aureus* occurred in 100-120 minutes.

Example 3—Vaporized Hydrogen Peroxide (VHF)

An alternative method of applying the hydrogen peroxide to the film is by exposure to vaporous hydrogen peroxide (VHP). After collecting data in Example 2, which showed that drying a PVP-HP solution into a film resulted in a concentration of the peroxide and antimicrobial activity, the object of the next experiment was to determine the oxidant potential of PVP in cast films after exposure to a VHP cycle. It was determined that PVP solutions (without peroxide solution) could be efficiently complexed with hydrogen peroxide by using VHP. With the use of this method, the hydrogen peroxide was readily available on the surface. Concentration may be varied by exposure time and/or concentration of hydrogen peroxide vapor.

Films were cast from 10% PVP of various molecular weights, prepared in methanol. A fixed volume of 1.2 mL was placed in a weight boat and allowed to dry. Pre- and post-sample weights were collected for use in calculations. The films were placed in an aluminum test chamber and exposed to 250 ppm VHP for 90 minutes. Films were immediately titrated to determine the total oxidant concentration.

Figure 5:
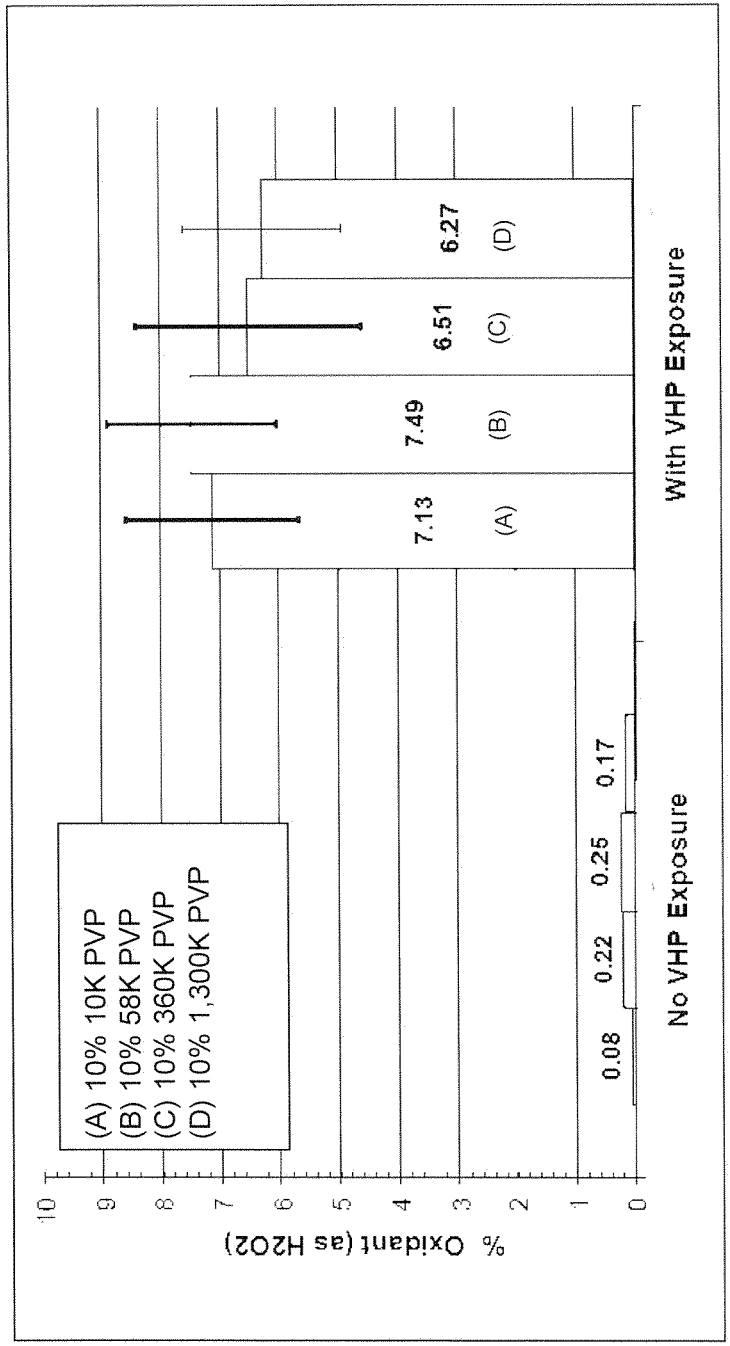
FIG. 5 reflects hydrogen peroxide concentration (as % oxidant) in crosslinked PVP films (of various molecular weights) wherein the film is activated using vaporous hydrogen peroxide (VHP) at 250 ppm VHP for ninety minutes as compared to PVP films without exposure to VHF).

Results are shown in FIG. 5 and showed that similar concentrations of oxidant were measured in all samples after exposure to a VHP cycle. Control samples without VHP exposure showed no oxidant potential.

Next, it was determined if the measured oxidant potential (peroxide) in the films translated to biocidal activity against bacteria.

PVP film coupons were prepared by drying a 10% solution of 58 K PVP in water or methanol and exposing the film to 400 ppm of VHP for 30 minutes. PVP-HP films were prepared by curing a solution of PVP-HP and water. And, a PVP film without peroxide inclusion (a control) was prepared. Films were challenged with 20 µL of a neat culture of a buffered suspension of *S. aureus* ATCC 6538, a 10-fold dilution of the culture or a 100-fold dilution of the culture. Inoculum was added at $t_0$, and contact times were 1, 2, 3, 4 and 5 hours (neat culture) or 6, 12, 18, 24 and 30 minutes for dilute cultures. All coupons were covered to protect them from over-drying between samplings. To neutralize, coupons were transferred to a glass containing 10 ml of LAT broth (1% v/v catalase), vortexed briefly, sonicated for 5 minutes, vortexed again for 30 seconds and sampled. Dilutions were pour-plated with LAT agar and incubated for 3 days at 37° C.

Figure 6:
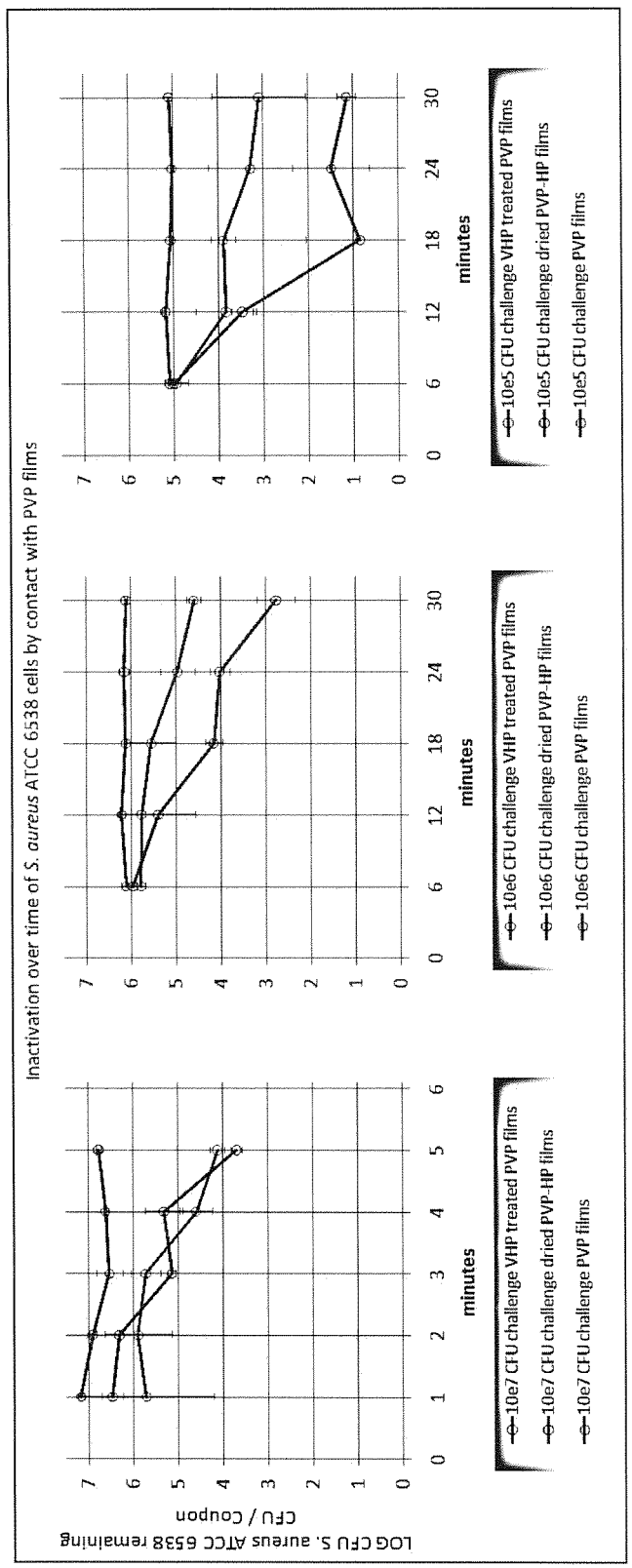
FIG. 6 reflects inactivation (log reduction) over time of *S. aureus* ATCC 6538 cells in contact with VHP-treated PVP films, PVP-HP dried films (from solution), and PVP films (no active).

Results are shown in FIG. 6 and demonstrated that cast PVP-HP films treated with hydrogen peroxide by two different methods provided biocidal activity, while PVP films not treated with hydrogen peroxide showed no microbial activity.

Figure 7:
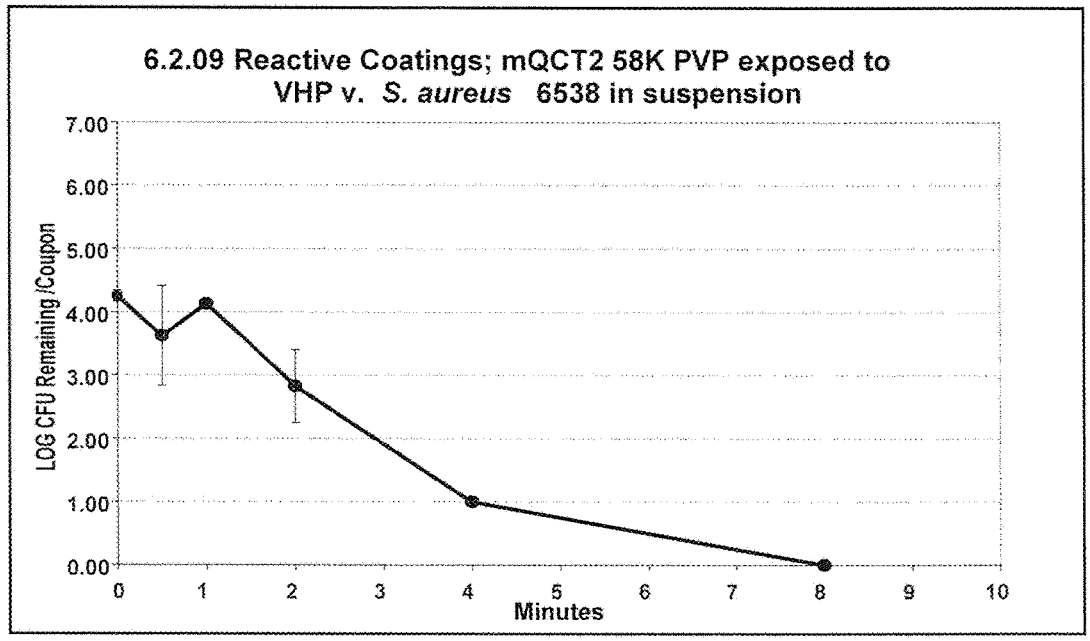
FIG. 7 reflects log reductions of *S. aureus* ATCC 6538 for 58 K PVP films exposed to VHP.

Microbiological surface testing (mQCT2) of the 58 K PVP exposed to VHP samples showed a 4 LOG reduction (complete kill) against *S. aureus* in 80 minutes, see FIG. 7.

Discs of dried 10% 58K PVP films were exposed to VHP and then challenged with $10^4$ CFU *B. subtilis* 19659 spores delivered as a 20 µL buffer suspension. Inoculum was added at $t_0$, and sampling times were 20, 40, 90, 150 and 300 minutes. To neutralize, discs were transferred to glass culture tubes, washed with 10 mL of LAT broth (1% v/v catalase), vortexed briefly, sonicated for 5 minutes, vortexed briefly again, and then sampled. Dilutions were pour-plated with LAT agar and incubated for 2 days at 37° C.

Figure 8:
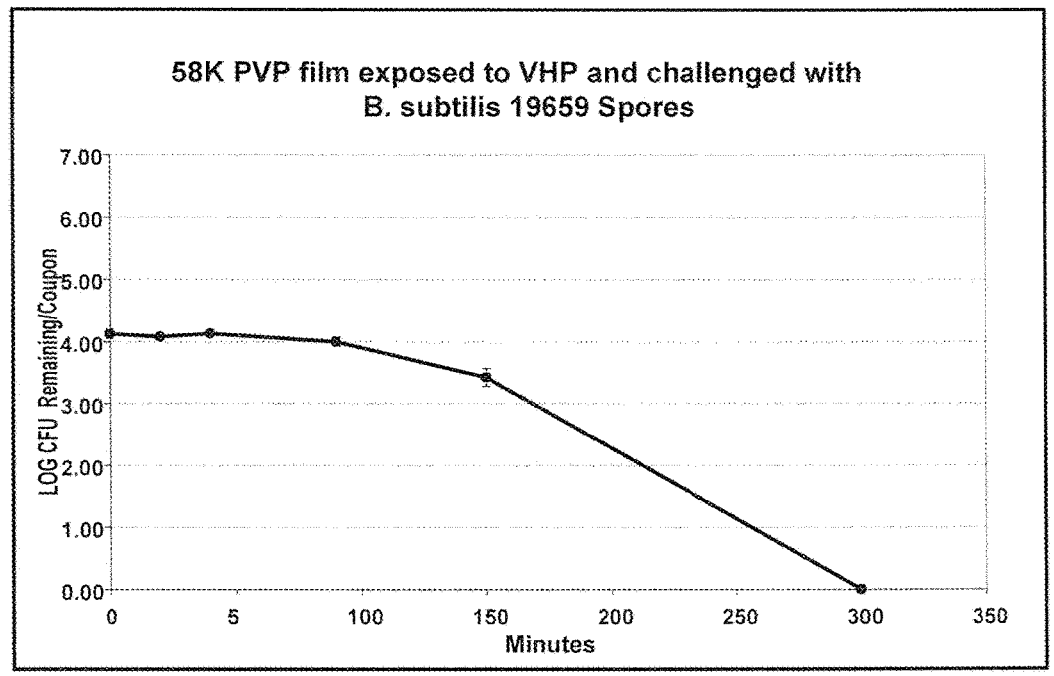
FIG. 8 reflects log reduction of *B. subtilis* ATCC 19659 spores for 58 K PVP films exposed to VHP.

The results are shown in FIG. 8. A 4 log kill of *B. Subtilis* (complete kill) occurred in approximately 5 hours or 300 minutes.

Unexpectedly, these results established that the kill time achieved for *S. aureus* above was much shorter than for any other known reactive surface/coating. The sporicidal efficacy of the invention achieved was also quite significant and is rarely cited in any reports on reactive surfaces.

Both examples 2 and 3, above, confirmed that hydrogen peroxide in PVP films provided antimicrobial activity, while PVP films not treated with hydrogen peroxide showed no antimicrobial activity.

Example 4—Effect of Crosslinking

To provide an insoluble surface, PVC was crosslinked. As discussed above, this can be accomplished numerous ways including with the use of initiators and UV light. For this example, the method used was UV light; of particular interest was UVC in the range from 250-260 nm. PVP with a high molecular weight, 360 K-1300 K, was indicated in the literature to product the best crosslinked properties. Testing confirmed this.

Solutions of a 10% (w/w) 1,300,000 K (1300 K) mw PVP were prepared with 20-50 mM of hydrogen peroxide added to catalyze the crosslinking reaction. This solution was applied to surfaces for crosslinking by volume. Example surfaces were: Teflon coated septum from GC vial caps, cloth and fabrics, painted surfaces including the military CARC and glass. The UV apparatus had four 24 W UV lights mounted in parallel. The distance from the lights to the base on which the samples are set was 5 cm. The energy density in the UVC range was >100 mJ/min, and exposure time was two hours.

Percent crosslinking of samples was determined on a weight basis. Crosslinked PVP will swell when exposed to water, but will not dissolve. Therefore, samples were placed in water for 24-72 hours after crosslinking occurred. This allowed the uncrosslinked PVP to go into solution while the crosslinked portion remained intact. The sample was then filtered to capture only the crosslinked portion, and was dried to 50° C. for 24 hours to remove all moisture. The difference in weight of the PVP used to make the sample and the weight of crosslinked PVP provided a measurement of the percent PVP that was crosslinked. This is termed percent gel or percent crosslinking in the literature.

Figure 9:
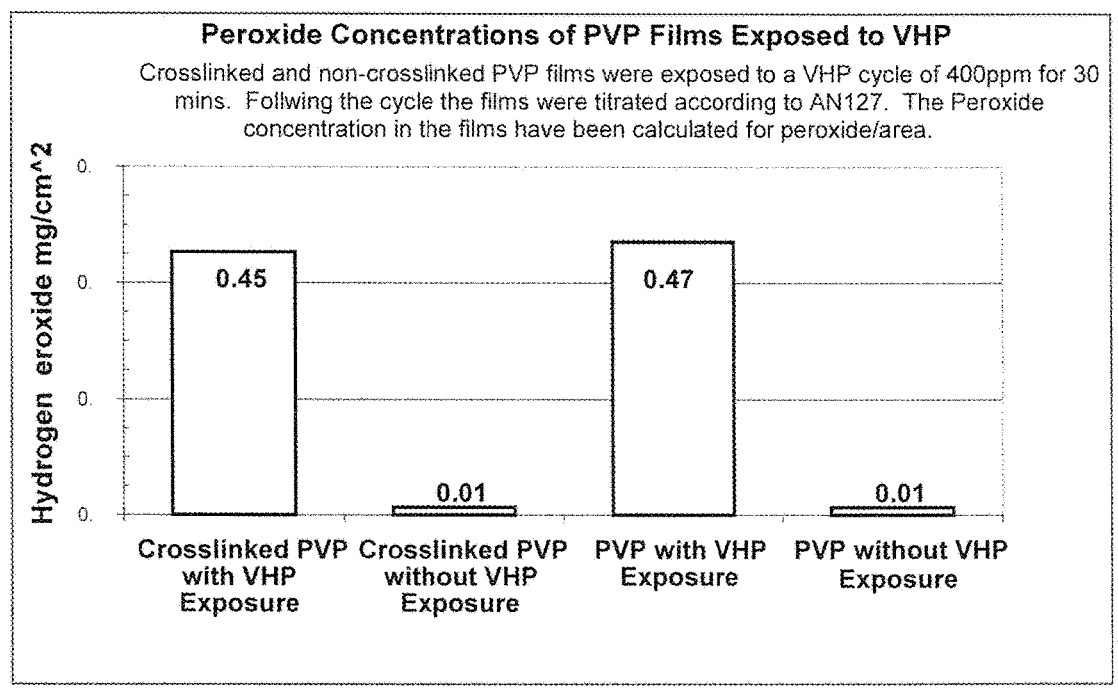
FIG. 9 reflects hydrogen peroxide concentration (mg/cm$^2$) of crosslinked and non-crosslinked PVP films with or without exposure to a VHP cycle of 400 ppm for 30 minutes.

The uptake of hydrogen peroxide by vapor exposure (activation of the surface, expressed as mg/cm$^2$) was the same for crosslinked or uncrosslinked samples. See FIG. 9.

Films were cast in inverted Viton GC vial caps ~1.3 cm$^2$ in area. The samples were prepared with the following compositions: 1300 K cross-linked PVP exposed to VHP 400 ppm 30 minutes; 1300 K cross-linked PVP; 1300 K non-cross-linked PVP exposed to VHP 400 ppm 30 minutes; and 1300 K non-cross-linked PVP. The samples were challenged with 10$^5$ CFU of S. aureus ATCC 6538 delivered as a buffered suspension.

Activity was assessed in two ways: 1) liquid inoculum was added at $t_0$, contact times were 10, 20, 40, 80 and 160 minutes, and 2) liquid inoculum was added at $t_0$, and contact times were every 2.5 minutes from 40 to 87.5 minutes. To neutralize, samples were transferred to glass culture tubes filled with 10 mL of LAT broth (1% v/v catalase), vortexed briefly, sonicated for 5 minutes, vortexed briefly again, and then sampled. Dilutions were pour-plated with LAT agar and incubated for 1 day at 37° C. and 1 day at 30° C.

Figure 10:
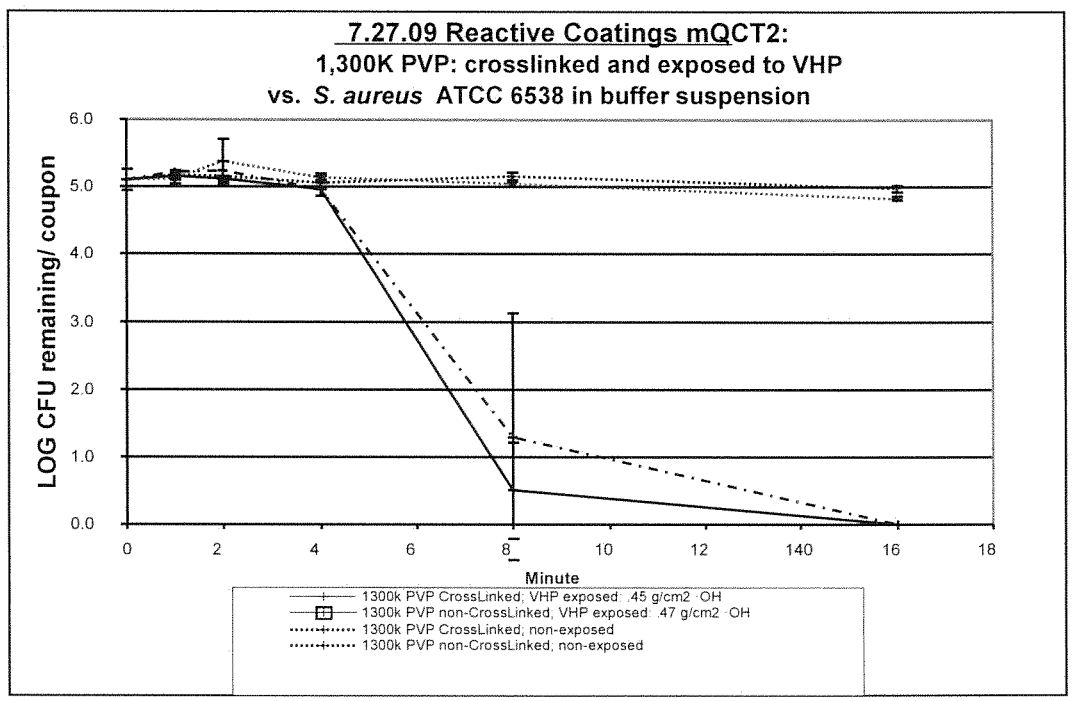
FIG. 10 reflects log reductions of *S. aureus* ATCC 6538 in a 1300 K PVP crosslinked film exposed to VHP.

Results are shown in FIG. 10. The cross-linked film proved to be effective with performance equivalent (at this timescale) to a non-cross-linked control. The 1300 K cross-linked insoluble PVP film exposed to VHP was predicted to inactivate the challenge in 80.34 minutes. The non-cross-linked PVP film exposed to VHP was predicted to achieve complete kill in 77.12 minutes. Practically, this testing showed no difference between the two types of surfaces (cross-linked vs. non-cross-linked) and their ability to react with and inactivate S. aureus ATCC 6538. The kill time achieved for S. aureus is much shorter than any other known reactive surface/coating.

Example 5—Activity of Cross-Linked PVP-HP Films Against Spores

To determine whether PVP-HP films retain their biocidal characteristics over time, 1300 K cross-linked PVP films were exposed to VHP and then their sporicidal activity was assessed.

A modified QCT2 was performed, challenging 1300 K cross-linked PVP exposed to VHP with $10^{6.0}$, $10^{5.5}$, $10^{5.0}$, $10^{4.5}$ and $10^{4.0}$ CFU of B. Subtilis 19659 spores delivered as 20 µL of buffer suspension. Films were prepared in inverted Viton GC vial caps and measured ~1.3 cm$^2$ in area. Activity was assessed in two ways: 1) Inoculum was added at $t_0$ and contact times were 20, 40, 90, 150 and 300 minutes and 2) Inoculum was added at $t_0$ and contact times were 15, 30 and 45 minutes and every hour from 1 to 12 hours. To neutralize, caps were transferred to glass culture tubes filled with 10 mL of LAT broth (1% v/v catalase) from a syringe, vortexed briefly, sonicated for 5 minutes, vortexed briefly again, and then sampled. Dilutions were pour-plated with LAT agar and incubated for 2 days at 30° C.

Figure 11:
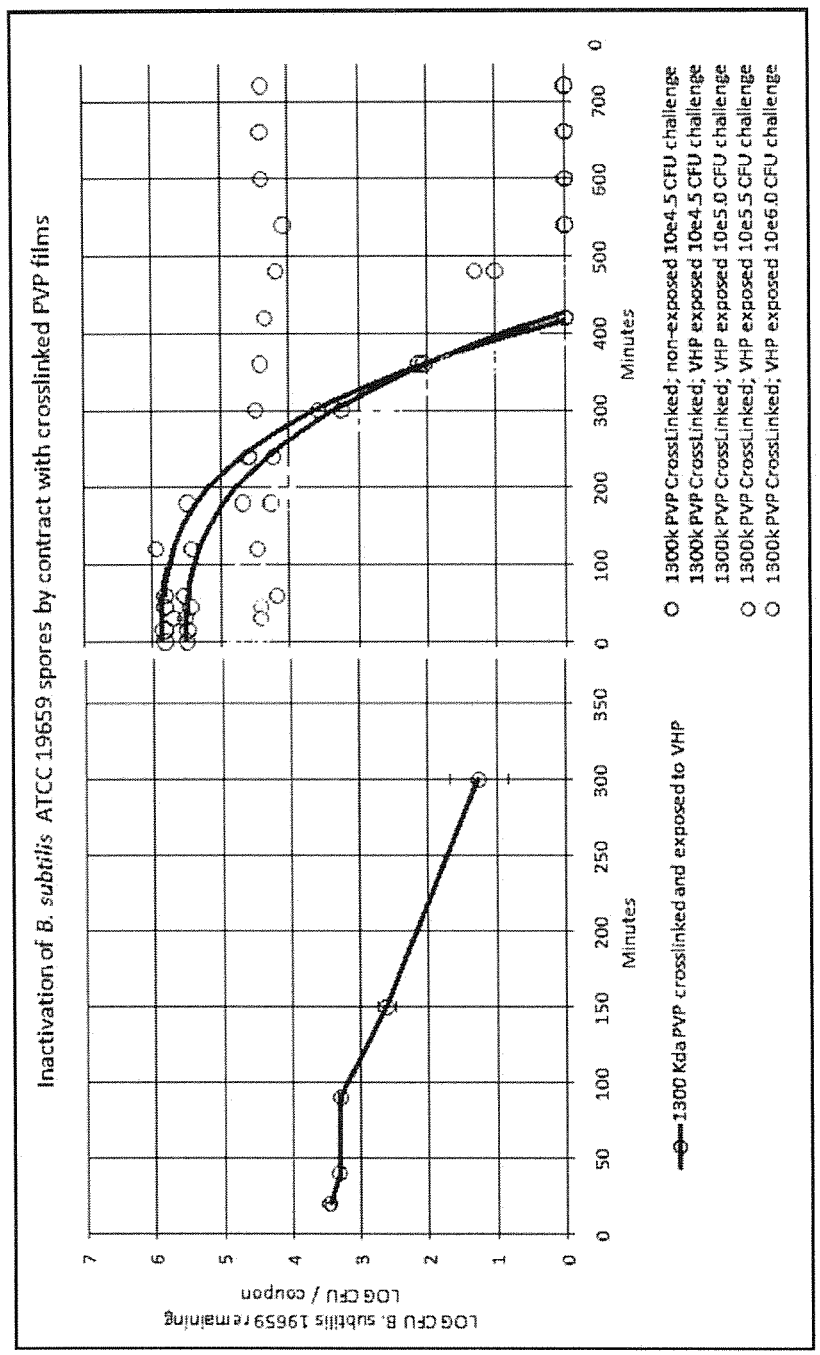
FIG. 11 reflects inactivation (log reduction) of various loads of *B. subtilis* ATCC 19659 spores by contact with 1300 K PVP crosslinked films exposed to VHP and not exposed.

Results (FIG. 11) showed that all five spore challenge levels, tested on two different occasions, were inactivated between 6 and 7 hours, with an average estimated activation time of 6 hours and 40 minutes (as assessed by GInaFiT, a freeware tool useful to assess non-log-linear microbial survivor curves). This data indicated that cross-linked PVP treated with VHP is very active as a sporicide.

Example 6—Activity of Cross-Linked PVP-HP Against Spore and Non-Spore-Forming Military and Healthcare Relevant Species Due to the success achieved with S. aureus and B. subtilis, a variety of microbiological organisms were tested against the UV crosslinked 1300 K PVP film with a 30 minute exposure time to 400 ppm VHP.

1300 K cross-linked PVP was exposed to VHP then challenged with 20 µL of various inocula targeting 10$^5$ CFU. Spore-forming species were re-suspended and diluted in buffer. Vegetative organisms were re-suspended and diluted in 0.1% peptone buffer. Films were prepared in inverted Viton GC vials caps and measured ~1.3 cm$^2$ in area. Inoculum was added at $t_0$. Contact times were 30, 60 and 90-minutes for vegetative organisms and 3, 6 and 9 hours for spore-forming organisms. To neutralize, caps were transferred to glass culture tubes filled with 10 mL of LAT broth (1% v/v catalase), vortexed briefly, sonicated for 5 minutes, vortexed briefly again, and then sampled. Dilutions were pour-plated with LAT, SDA or RCM agars as appropriate and incubated for 2 days at 37° C. or 30° C. as appropriate.

The data set forth in Table 2 below show the organisms tested and the results obtained. The data demonstrated that 1300 K cross-linked PVP provided excellent broad-spectrum capability against both vegetative (non-spore forming) and spore-forming species. The highest log reduction was not always at the longest contact time because several organisms lost viability over the course of the experiment, which in the table appear as LOG reduction values that decrease with time.

TABLE 2

Broad-Spectrum Efficacy of 1300K Crosslinked PVP Exposed to Vaporous Hydrogen Peroxide

| OD | Organism (Vegetative) | % Red 30 min. | LRed 30 min. | % Red 60 min. | Log R 60 min. | % Red 90 min. | LogR 90 min. |
|---|---|---|---|---|---|---|---|
| 0.992 | S. choleraesius 10708 | 99.9993* | 5.13* | 99.9980 | 4.71 | 99.9993 | 5.18 |
| 0.998 | A. Baumanii 19606 | 99.9992* | 5.11* | 99.9989 | 4.96 | 99.9974 | 4.58 |
| 1.030 | K. pneumophilia 4352 | 99.9990* | 5* | 99.9979 | 4.67 | 99.9979 | 4.69 |
| 1.050 | P. aeruginosa 9027 | 99.9981* | 4.73 | 99.9953 | 4.33 | 99.9833 | 3.78 |
| 0.000 | B. cepacia 35254 | 99.9820 | 3.74 | 93.0664 | 1.16 | <99 | <2 |
| 1.050 | K. oxytoca 8724 | 99.9816 | 3.73 | 99.9690 | 3.51 | 99.9245 | 3.12 |
| 1.017 | L. monocytogenes 35152 | <99 | <2 | 99.9988* | 4.93 | 99.9987 | 4.89 |
| 1.081 | ESBL E. coli BAA 196 | <99 | <2 | 99.9984* | 4.79* | 99.9981 | 4.72 |
| 1.011 | Y. entercolitica 9601 | 99.9740 | 3.59 | 99.9982* | 4.74* | 99.9976 | 4.61 |
| 1.050 | E. coli 0157:H7 | <99 | <2 | 99.9992 | 5.09 | 99.9998* | 5.75* |
| 1.090 | Ca MRSA USA 300 | 99 | <2 | 99.9938 | 4.21 | 99.9993* | 5.13* |
| xxxx | S. aureus 6538 | <99 | <2 | <99 | <2 | 99.9990* | 5* |
| 0.983 | MRSa 33591 | 99.5359 | 2.33 | 99.6154 | 2.42 | 99.9985* | 4.82* |
| 1.060 | VISA CV 482 | <99 | <2 | 99.4661 | 2.27 | 99.9808* | 3.72* |
| 1.060 | C. albicans 10231 | 90.2446 | 1.01 | 99.9271 | 3.14 | 99.9713* | 3.54* |

| OD | ORGANISM (spore-forming) | 3 hours | | 6 hours | | 9 hours | |
|---|---|---|---|---|---|---|---|
| 0.066 | B. cereus 14579 | 99.9981* | 4.71* | 99.7688 | 2.64 | 99.9951 | 4.31 |
| 0.014 | B. sphericus 14577 | 99.9945* | 4.26* | 99.9713 | 3.54 | 99.9693 | 3.51 |
| 0.080 | S. chartarum 16275 | 99.8194* | 2.74* | 99.0894 | 2.04 | 98.3928 | 1.79 |
| 0.022 | A. niger 16404 | 99.5626* | 2.36* | 98.9817 | 1.99 | 97.4302 | 1.59 |
| 0.640 | B. megaterium 14581 | <99 | ?2 | 99.9975* | 4.6* | 99.9939 | 4.21 |
| 0.300 | C. difficile | 99.9607 | 3.41 | 99.9920* | 4.1* | 99.9446 | 3.26 |
| 0.247 | G. stearothermophilus 7953 | <99 | <2 | 99.9842* | 3.8* | 99.8153 | 2.73 |
| xxxx | B. subtilis 19659 | <99 | <2 | 99.9224 | 3.11 | 99.9985* | 4.81* |

*indicates complete kill at this time point
% Red = % Reduction
LogR = Log Reduction

Example 7—Efficacy Against Live Biological Warfare Agent

Durable PVP-HP surfaces with antimicrobial activity proved effective against a variety of non-spore-forming and spore-forming bacteria. In this example, PVP-HP film was challenged with live biological warfare agent *Bacillus anthracis* (Ames strain).

Films exposed or not exposed to VHP were challenged with $10^5$ CFU B. anthracis (Ames strain) as 20 µL of buffer suspension. Films were prepared in inverted Viton GC vial caps and measured ~1.3 cm² in area. Inoculum was added at $t_0$. Contact times were 15, 30, 45, 60, 90, 120, 150, 180, 210, 240, 270, 300, 330, 360 and 420 minutes. To neutralize, coupons were transferred to glass culture tubes filled with 10 mL LAT broth (1% v/v catalase), vortexed briefly, sonicated for 5 minutes, vortexed briefly again and then sampled.

Figure 12:
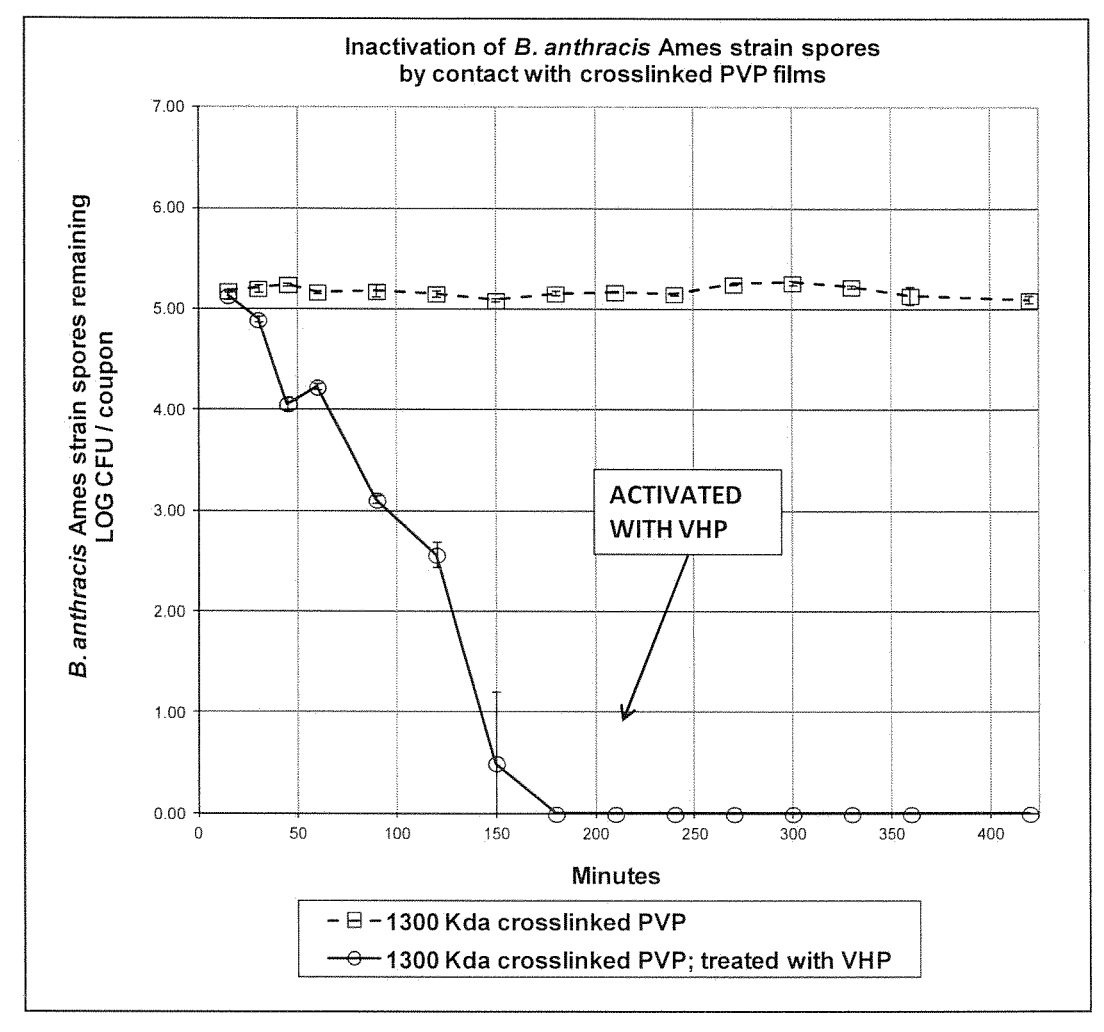

Results as reflected in FIG. 12 showed that spores of the live biological warfare agent *B. anthracis* (Ames strain) were a less stringent challenge than the surrogate *B. subtilis* ATCC 19589 spores. 1300K PVP completely inactivated $10^5$ *B. anthracis* (Ames) spores in 2 and ¾ hours.

Example 8—Oxidant Potential of Cross-Linked PVP on Military Surfaces After VHP Exposure A methodology was developed to cross-link PVP directly onto relevant military surfaces. Insoluble cross-linked PVP films on military surfaces were shown to be biologically active, with oxidation potential consistent with those values previously observed with lab-based films (Example 4).

A study was conducted on 1300 K cross-linked PVP on a variety of surfaces to evaluate the consistency of the oxidant potential on a variety of surfaces. Films were created using 1300 K PVP and the previously described UV cross-linking method (Example 4). The samples were exposed to 400 ppm VHP for 30 minutes. The GC caps and the CARC panels were exposed on one side. The polyester wipes were skewered and exposed to VHP on both sides. The oxidant level was determined using a thiosulfate titration. The wipes had twice the surface area exposed to the VHP and this was accounted for in the surface area calculation.

Figure 13:
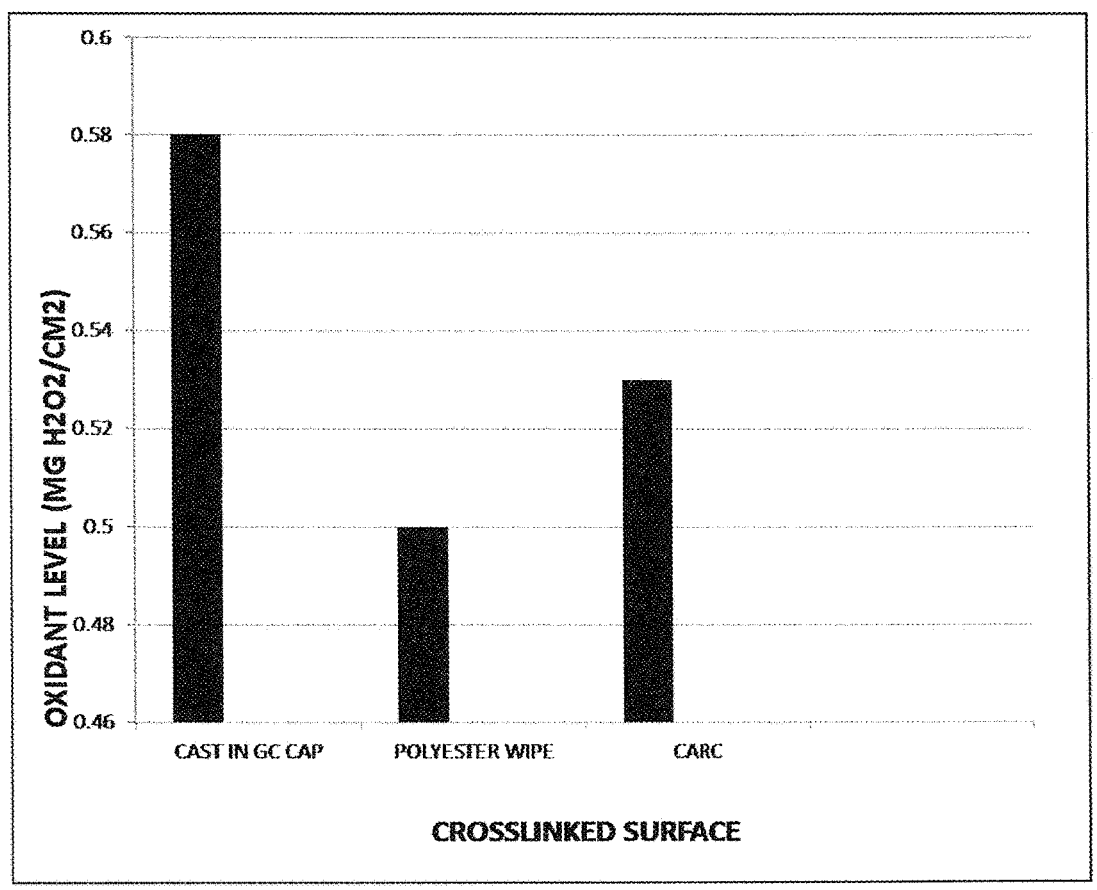
FIG. 13 reflects measured oxidant levels (mg $H_2O_2$/cm$^2$) of a crosslinked PVP surface (3 different substrates) after VHP exposure.

The results shown in FIG. 13 reflect that oxidant potential after exposure to a VHP cycle is consistent across the military relevant surfaces tested. Most exposures of PVP to VHP resulted in 0.4-0.6 mg/cm² hydrogen peroxide.

Example 9—Efficacy of PVP/HP Films Incorporated onto a Military Surface Through Cross-Linking Cross-linked PVP-HP films were shown to be a water insoluble coating that afforded high decontamination efficacy against a variety of spore-forming and non-spore-forming microbial challenges including the live biological warfare agent *B. anthracis* (Ames strain) (Example 7). A methodology was developed to cross-link PVP directly onto surfaces. In this example, the ability of PVP cross-linked onto the surface of a CARC (chemical agent resistant coating) painted aluminum panel to inactivate *S. aureus* ATCC 6538 was evaluated.

1300K cross-linked PVP was prepared on CARC painted aluminum panels and exposed to VHP. The panels were then challenged with $10^5$ CFU of *S. aureus* ATCC 6538 delivered as 20 µL of suspension. Films measured ~19.6 cm² in area.

Each coupon was placed in a sterile 250 ml cup and inoculum was added at $t_0$. Contact times were 7, 15, 24, 34, 45, 57, 70 and 84 minutes. To neutralize, each coupon was washed in its sup with 20 mL of LAT broth (1% v/v catalase). The cup containing the coupon and neutralizer was then swirled briefly and covered with parafilm. Covered cups were sonicated for five minutes, vortexed briefly, and then sampled. Cups that could not be immediately sonicated were kept at 4° C. Dilutions were pour-plated with LAT agar and incubated for 2 days at 37° C.

Figure 14:
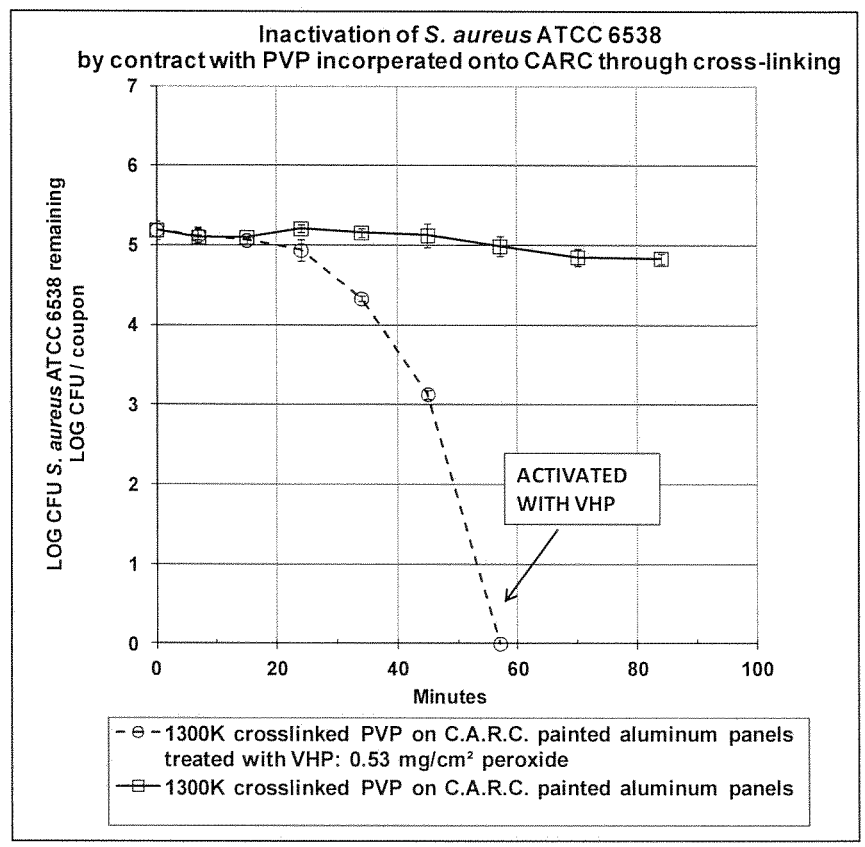
FIG. 14 reflects inactivation (log reduction) of *S. aureus* ATCC 6538 by contact with PVP incorporated on CARC painted aluminum panels through crosslinking, followed by VHP exposure to yield 0.53 mg/cm$^2$ peroxide.

FIG. 14 reflects the data obtained. Complete inactivation of $10^5$ S. aureus ATCC 6538 was seen before 60 minutes of contact with the PVP film incorporated on the CARC-painted panel, which is 20 minutes shorter than the inactivation achieved with the coating on GC vial caps. This data provides strong evidence for the tenability of direct incorporation of PVP onto military relevant surfaces through cross-linking.

Example 10—Efficacy Against B. subtilis Spores of PVP Cross-Linked Onto a CARC Surface In this example, the ability of PVP cross-linked onto the surface of CARC painted aluminum panels to inactivate B. subtilis ATCC 19659 spores was evaluated. 1300K cross-linked PVP was prepared on CARC painted aluminum panels and exposed to VHP. The panels were then challenged with $10^5$ CFU of B. subtilis ATCC 19659 spores delivered as 20 μL of suspension. Films measured ~19.6 cm² in area. Each coupon was placed in a sterile 250 mL cup and inoculum was added at $t_0$. Contact times were 20, 40, 60, 120, 180, 240, 300 and 360 minutes. To neutralize, each coupon was washed in its cup with 20 mL of LAT broth (1% catalase). The cup containing the coupon and neutralizer was then swirled briefly and covered with parafilm. Covered cups were sonicated for five minutes, vortexed briefly, and then sampled. Cups that could not be immediately sonicated were kept at 4° C. Dilutions were pour-plated with LAT agar and incubated for 2 days at 37° C.

Figure 15:
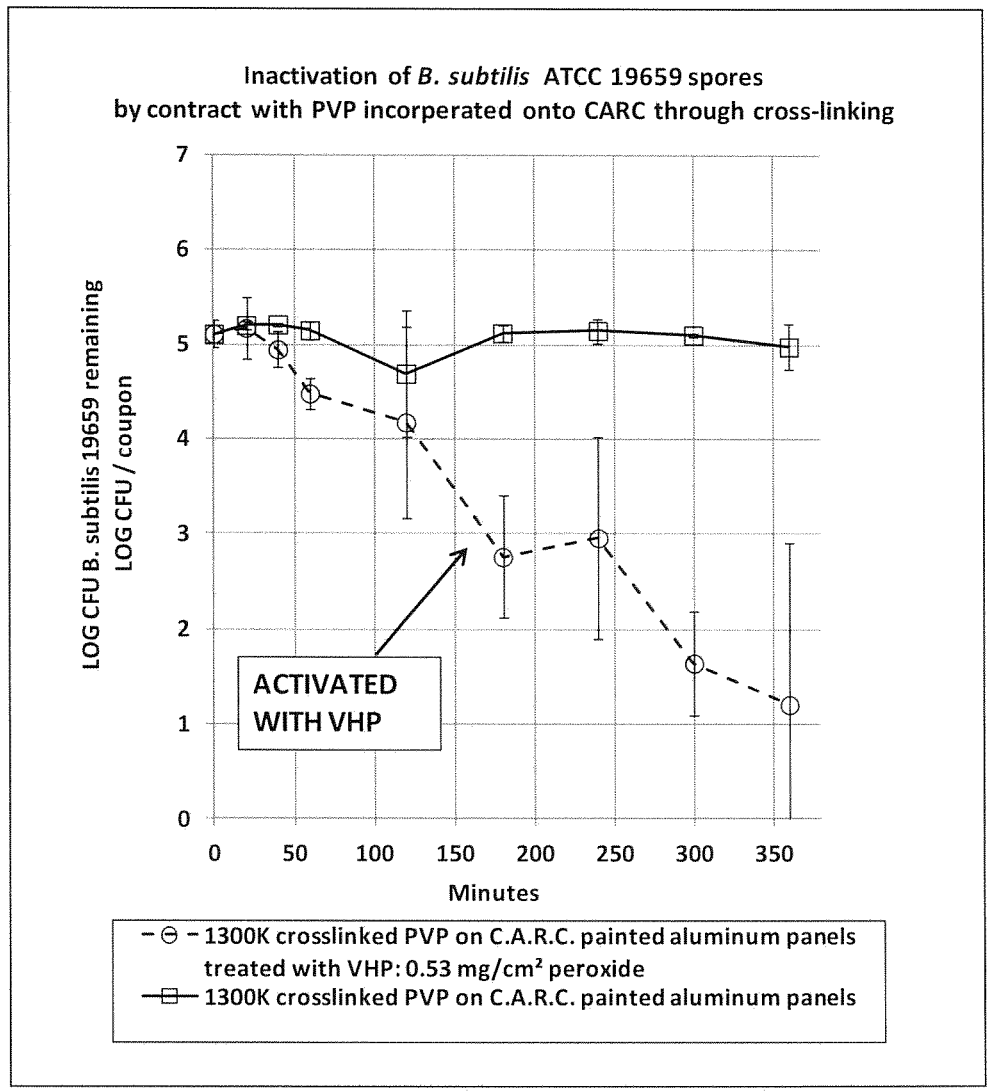
FIG. 15 reflects inactivation (log reduction) of *B. subtilis* ATCC 19659 spores by contact with PVP incorporated on CARC painted aluminum panels through crosslinking, followed by VHP exposure to yield 0.53 mg/cm$^2$ peroxide.

Results achieved are depicted in FIG. 15. Based on the data, inactivation of $10^5$ B. subtilis ATCC 19659 spores is predicted to occur around 7 and ½ hours, which is 1 and ½ hours longer than predicted for the same coating prepared in ~1.3 cm² GC caps. This data provided yet additional evidence that direct incorporation of PVP onto military relevant surfaces through cross-linking would provide microbiocidal activity.

Example 11—Efficacy Against B. anthracis (Ames) of PVP Cross-Linked Onto a CARC Surface Following on the above example 7, this example evaluated the ability of two film/substrate combinations to inactivate spores of the live biological warfare agent Bacillus anthracis (Ames). PVP cross-linked onto the surface of CARC painted aluminum panels and PVP cross-linked onto the surface of a wipe substrate were evaluated.

1300 K PVP cross-linked onto CARC panels or wipe substrate, and exposed or not exposed to VHP, were challenged with $10^5$ CFU B. anthracis (Ames strain) as 20 μL of buffer suspension. Inoculum was added at $t_0$. Contact times were 15, 30, 45, 60, 90, 120, 150, 180, 210, 240, 270, 300, 330, 360 and 420 minutes. To neutralize, coupons were transferred to glass culture tubes filled with 10 mL of LAT broth (1% v/v catalase), vortexed briefly, sonicated for 6 minutes, vortexed briefly again and then sampled.

Figure 16:
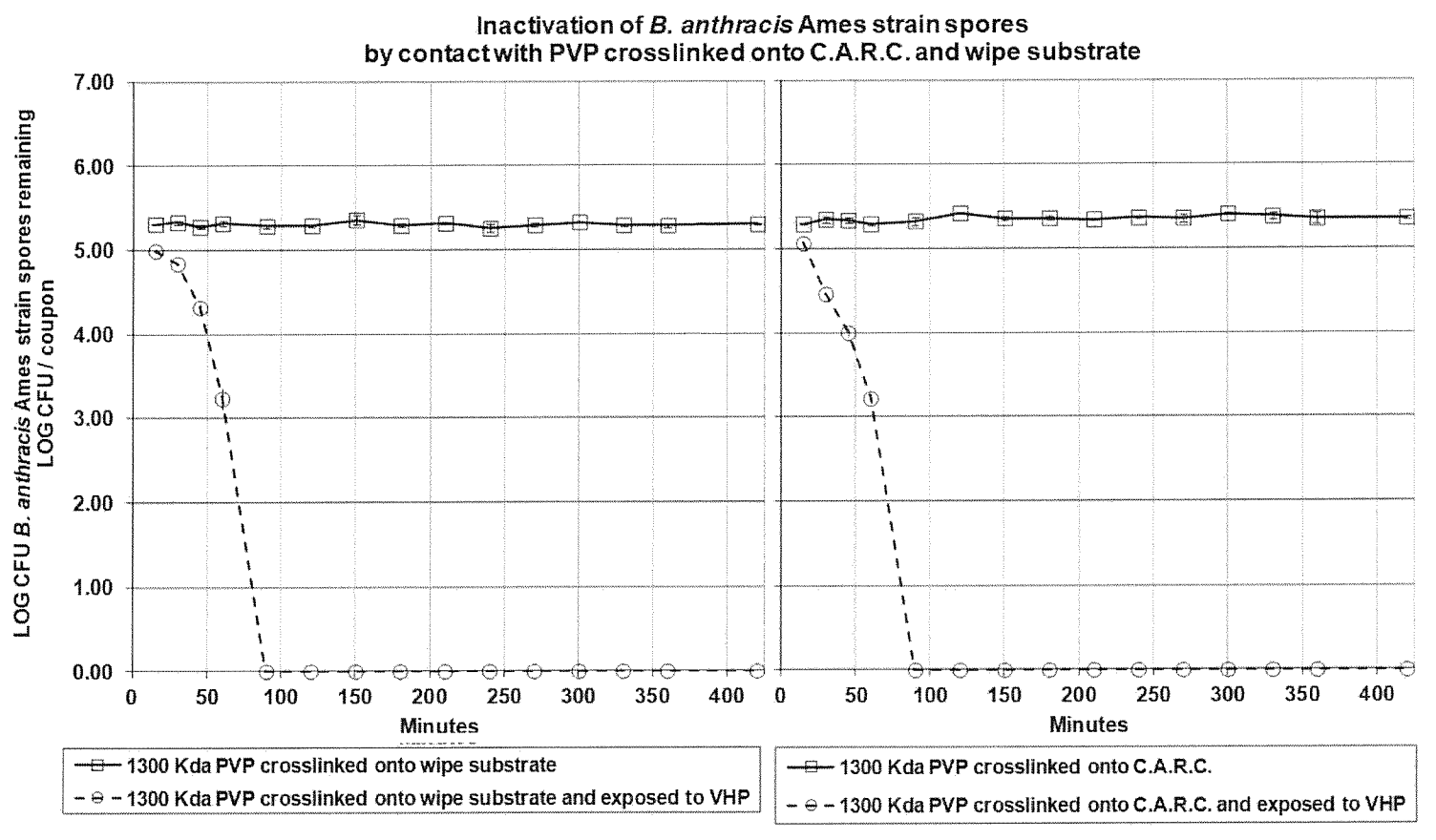

Results are shown in FIG. 16. The data indicates that complete inactivation of $10^5$ CFU of B. anthracis (Ames strain) spores required less than 90 minutes. As seen in the assessment of cross-linked PVP on GC vial caps (Example 7), B. anthracis (Ames strain) spores proved to be a much less stringent challenge than B. subtilis ATCC 19659 spores, providing again strong evidence for the tenability of direct incorporation of PVP onto military surfaces through cross-linking.

Examples 12-13—LDPE/PVP Extruded Films

The objective of Examples 12-13, below, was to evaluate the usability and durability of LDPE/PVP extruded films and to test them for their ability to absorb peroxide. A comparison of the peroxide absorption of select extrusion films to cross-linked PVP is set forth.

Example 12—Comparison of Different Extruded Films

A comparison was made between three different production methods for the formation of LDPE/PVP films by extrusion. The one-inch films were prepared on a lab-scale system. The four-inch wide strips were prepared on pilot scale equipment. One set of samples was prepared by dry mixing both components. The master batch samples were prepared from a pre-blend of pelletized 60/40 LDPE/PVP.

A comparison to the oxidation levels achieved with other non-soluble systems was performed. In this example, the cross-linked system was used for comparison. Additional studies showed that the molecular weight of the PVP used for extrusion did not change the absorption properties.

PVP films were prepared as previously described and exposed to a 400 ppm, 30 minute VHP decontamination cycle. One side of the cross-linked and non-cross-linked PVP films was exposed. LDPE/PVP films were exposed to VHP on two sides. Total oxidant was determined via titration. All concentration values are reported on a surface area basis.

Figure 17:
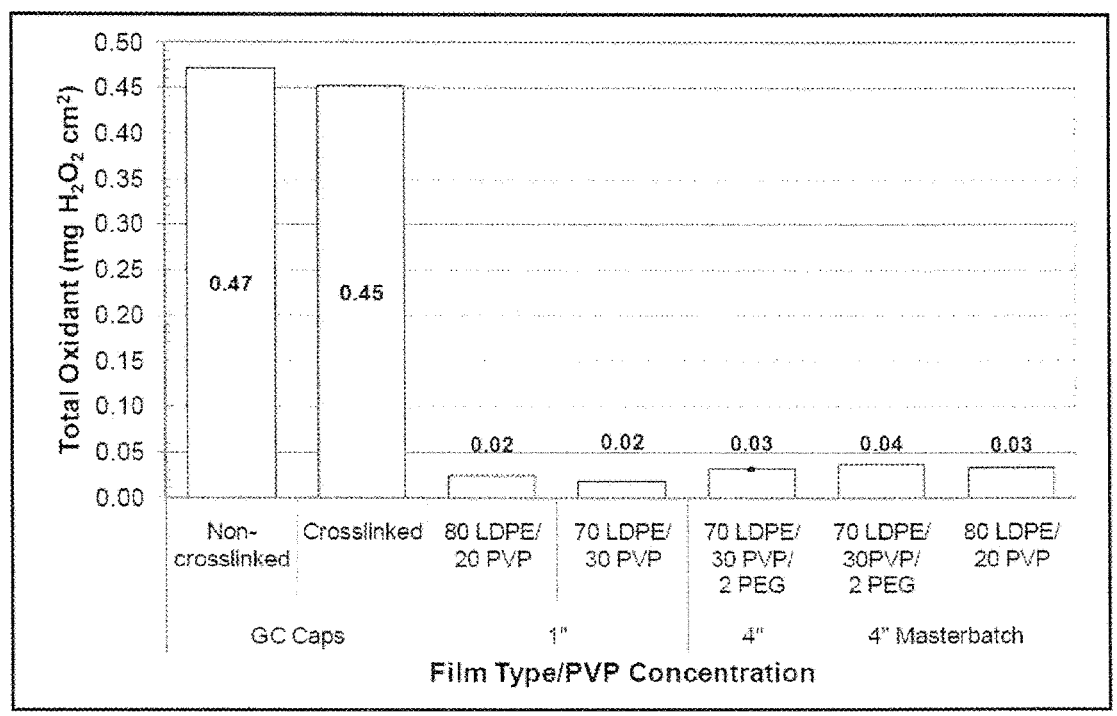
FIG. 17 reflects peroxide concentrations of several 1300 K PVP films: non-crosslinked, crosslinked, and blended with varying levels of LDPE after exposure to VHP.

The results are depicted in FIG. 17 and show that the LDPE/PVP system had much lower total oxidant potential than the PVP only systems. The values were not normalized to account for the difference in PVP concentration, as the evaluation was for the non-soluble systems in their designed form. It was also seen that the process by which the films were prepared had little effect on the amount of hydrogen peroxide absorbed through this process. Even though the values for total oxidant were low, the samples were tested for antimicrobial activity as set forth in Example 13.

Example 13—Gram Staining and Microscopic Examination of PVP/LDPE Films

The dispersion of the PVP in the LDPE film was explored, to try and elicit the reasons that excellent bacteriocidal activity was not achieved with these samples.

A section of LDPE/PVP 80/20 master blend film was stained by flooding with crystal violet stain for 1 minute followed by gentle rinsing with DI water, flooding with Gram's Iodine for 1 minute, followed by gentle rinsing with DI water, drop wise addition of clearing agent followed by gentle rinsing with DI water, flood with crystal violet followed by gentle rinsing with DI water, and finally blotting on bilious paper. Stained film and unstained control were viewed using a NIKON Ti-Eclipse inverted microscope using bright field illumination and using wide field fluorescence illumination with TEXAS RED and FITC emission/ excitation filter sets. Images were captured using Nikon elements. Bright field images were taken with 2 ms exposure. Fluorescence images were taken with 80 ms. exposure. Low magnification images were captured using a Droid 2 phone camera through a stereo microscope.

The results obtained are shown in FIG. 18. PVP and iodine complexes are often used as an antimicrobial preparation. Staining the prototype film with Gram-Iodine indicated the dispersion of PVP in the film and consequently revealed that the majority of the PVP was buried in the film and unavailable for staining. It was thought that the PVP was also unavailable for VHP uptake and for contact with spores and bacteria.

Gram's Iodine also fluoresces strongly under TEXAS RED ex/em, but not under FITC ex/em. PVP itself autofluoresces in FITC, so that all of the PVP could be seen in the sample. Combining these two signals, it is possible that the total PVP content of the film and the portion of the content available to the surface of the film could be determined and provide a valuable tool for film optimization.

Example 14—Evaluation of Surface Types

A reactive surface may be activated in two ways. One way is to incorporate both the activator and receptor into the surface simultaneously. The other is a two-step process in which the receptor is integrated into the surface and then the activator is applied. Both of these approaches were evaluated. Better results were achieved using the second method, where the activator was added as a secondary step as this effectively concentrated the active at the surface allow for better interactions with contaminants.

Films (GC caps and CARC panels) of 1300 K cross-linked PVP were exposed to a 400 ppm, 30 minute VHP decontaminations cycle and titrated for total oxidant (peroxide) concentration. Polyester wipes (with 1300 K PVP cross-linked) were skewered and exposed on both sides to VHP in the same manner. The calculation of concentration is reported in mg/cm$^2$ to account for the difference in exposure areas.

Figure 19:
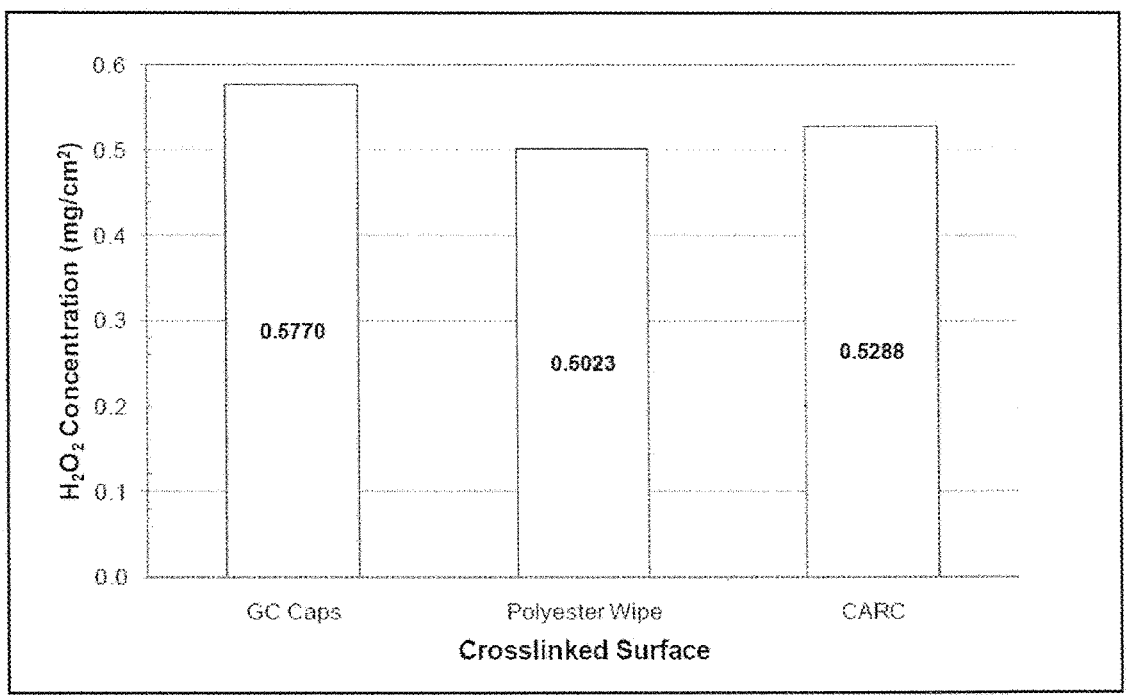
FIG. 19 reflects hydrogen peroxide levels (mg/cm$^2$) in 1300 K crosslinked PVP on various surfaces after VHP exposure.

FIG. 19 shows that regardless of surface type, absorption of the hydrogen peroxide by the cross-linked PVP was fairly uniform. On average, an exposure of the PVP to VHP resulted in a concentration of 0.4-0.6 mg/cm$^2$ of hydrogen peroxide.

Example 15—Use Life

In order to gauge the use life of cross-linked PVP-HP films, the sporicidal and microcidal activities of 1300 K cross-linked PVP films exposed to VHP one day to one week before being challenged were assessed.

1300K cross-linked PVP exposed to VHP was challenged with 10$^5$ CFU of S. aureus ATCC 6538 and B. subtilis ATCC 19659 spores, both delivered as 20 µL of buffer suspension. Films were prepared in inverted viton GC vial caps and measured ~1.3 cm$^2$ in area. Enough caps were prepared to run 3 iterations of the test. Caps were exposed to VHP one day before the first test, and testing commenced 1, 4 and 7 days post VHP exposure. In all cases, inoculum was added at t$_0$, contact times were 20, 40, 90, 180 and 360 minutes. To neutralize, caps were transferred to glass culture tubes filled with 10 mL of LAT broth (1% v/v catalase), vortexed briefly, sonicated for 5 minutes, vortexed briefly again, and then sampled. Dilutions were pour-plated with LAT agar and incubated for 2 days at 37° C.

Figure 20:
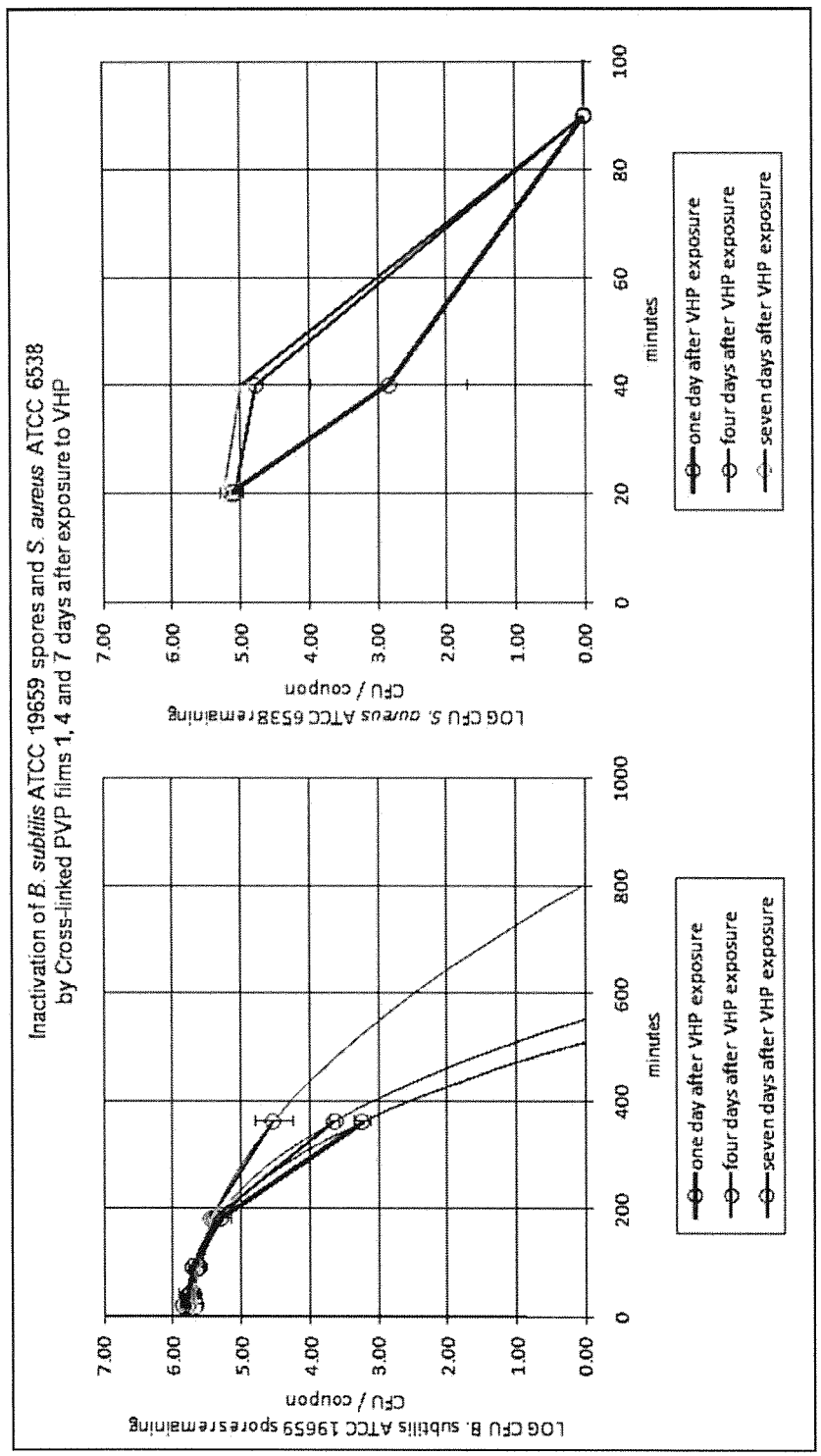
FIG. 20 reflects inactivation (log reduction) of both *B. subtilis* ATCC 19659 spores and *S. aureus* ATCC 6538 by crosslinked PVP films, one, four, and seven days after exposure to VHP.

Results in FIG. 20 showed that within one week, the sporicidal activity of all of the films only slightly diminished, despite losing over half of their peroxide content. This indicates that a fair amount of peroxide can be lost from the surface of the PVP coating while it remains efficacious against microorganisms.

Example 16—Regeneration Ability and Efficacy

Figure 21:
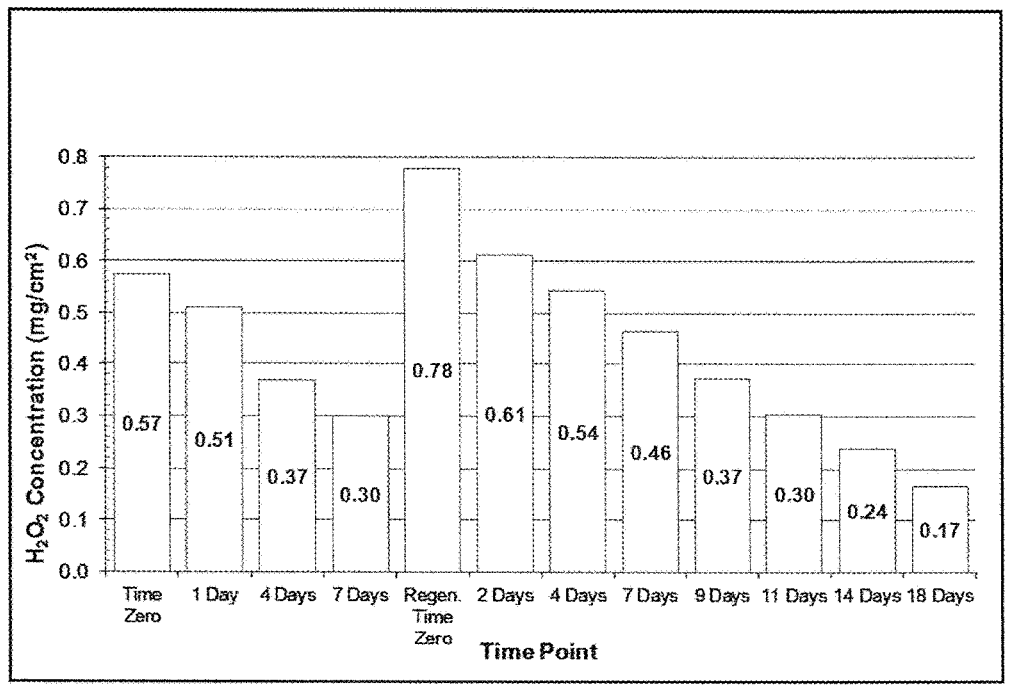
FIG. 21 reflects stability and regeneration of hydrogen peroxide in 1300 K crosslinked PVP films after exposure to 400 ppm, 30 minute VHP decontamination cycles at time zero and regeneration time zero.
Figure 22:
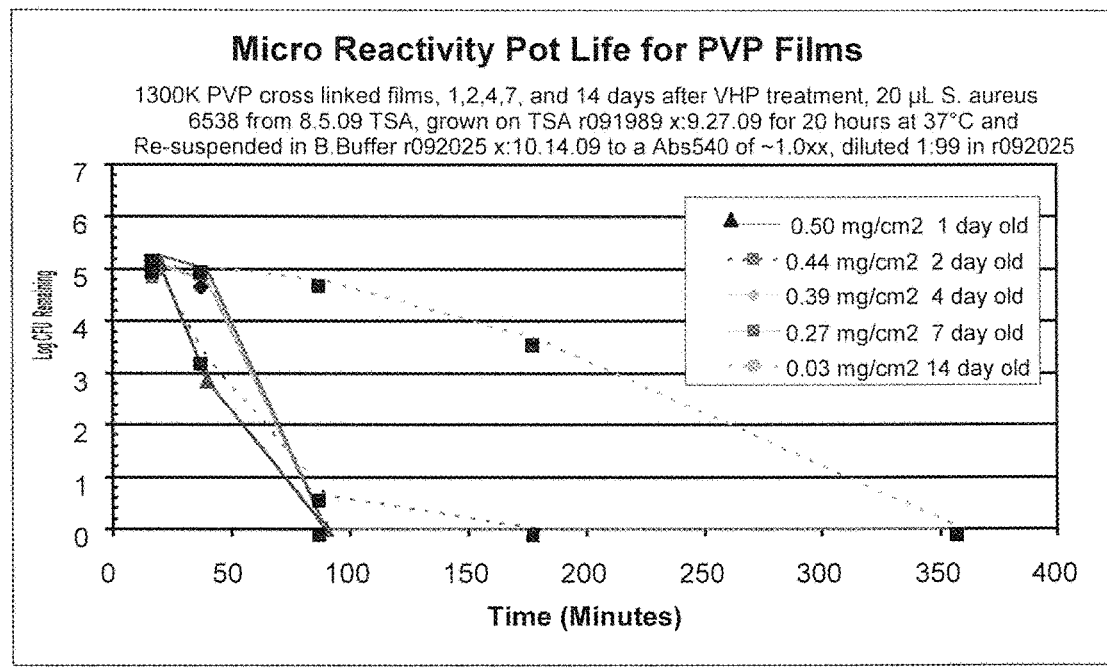
FIG. 22 reflects reactivity (log reduction) of 1300K PVP crosslinked films on days 1, 2, 4, 7, and 14 after VHP treatment using *S. aureus* ATCC 6538.
Figure 23:
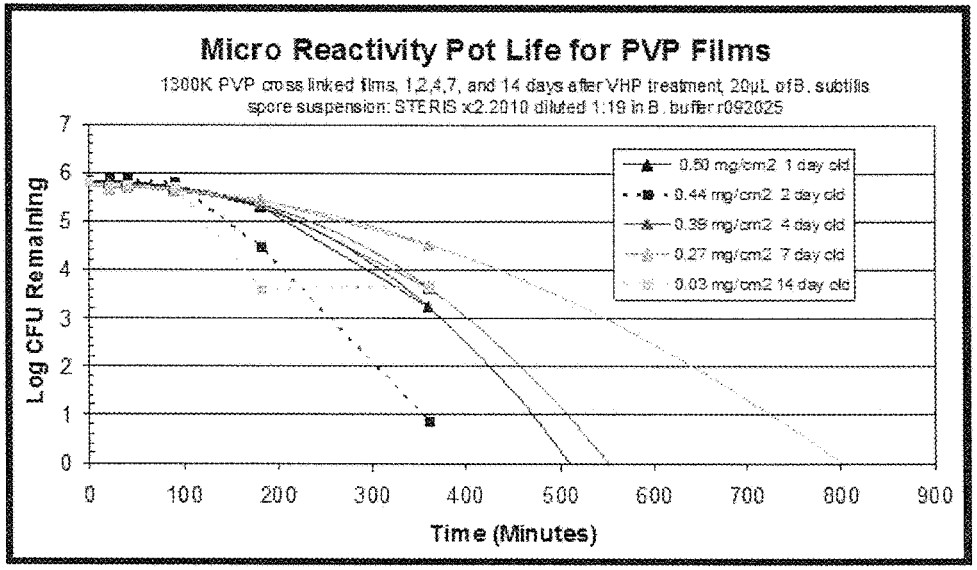
FIG. 23 reflects reactivity (log reduction) of 1300 K PVP crosslinked films on days 1, 2, 4, 7, and 14 after VHP treatment using *B. subtilis* ATCC 19659 spores.
Figure 24:
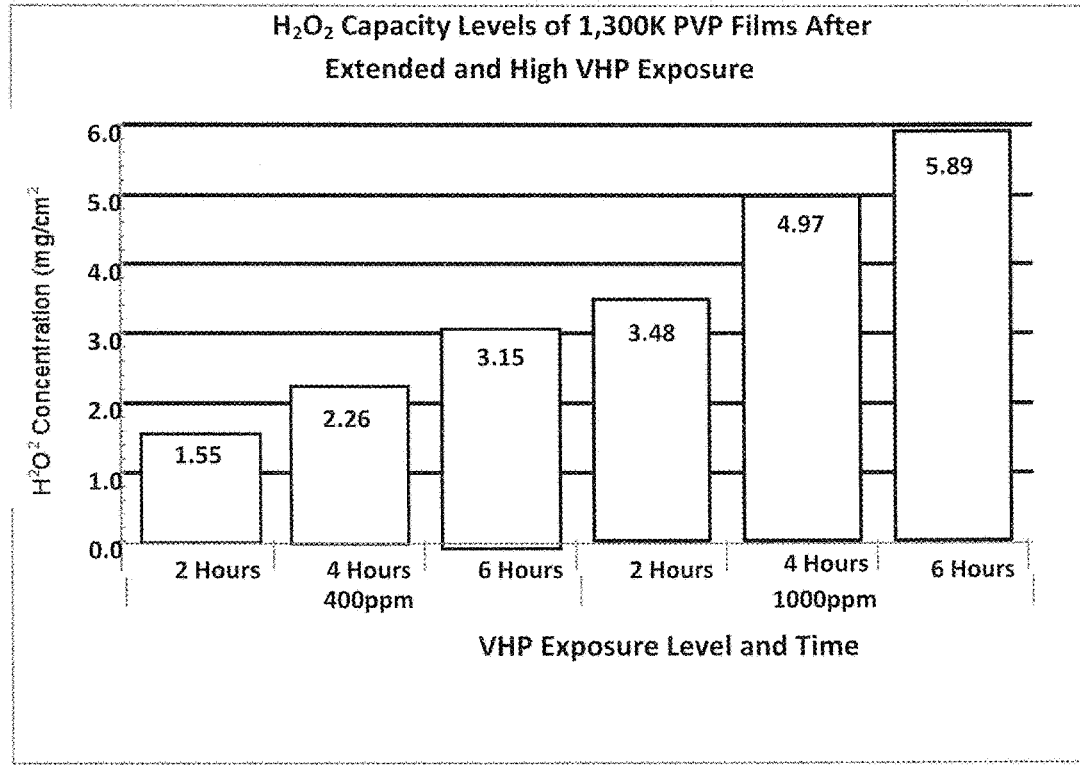
FIG. 24 reflects hydrogen peroxide concentration levels (mg/cm$^2$) of 1300 K PVP non-crosslinked films after extended and high VHP exposure.

Studies were performed to look at the regeneration abilities and the microbiological efficacy associated with the active, in this case hydrogen peroxide. Samples of 1300 K PVP cross-linked in Teflon coated GC vial caps were exposed to 400 ppm of VHP for 30 minutes. Typical values for hydrogen peroxide after exposure to a 400 ppm cycle for 30 minutes are 0.4-0.6 mg/cm$^2$. FIG. 21 shows the decay rate of the hydrogen peroxide over the first 7 days. After 7 days, the films were again exposed to 400 ppm of VHP for 30 minutes adding an additional ~0.5 mg/cm$^2$ of peroxide to the 0.3 mg/cm$^2$ still remaining after 7 days. The samples continued to be monitored through an additional two and a half weeks. Samples were stored exposed to air in a lab drawer. The amount of total oxidant was measured by thiosulfate titration at the times identified in FIG. 21. Each value reported was the average of five caps.

The results show that the decay rate for hydrogen peroxide is the same after the second VHP exposure as it was after the first exposure. This indicates the ability to regenerate the surface upon re-exposure to VHP, without affecting the active profile.

Microbiological testing was also performed in conjunction with the decay rate of the active. Testing was performed with both *S. aureus* (see FIG. 22) and *B. subtilis* (see FIG. 23). While active concentration decreased over the weeks monitored, this had little effect on the time to achieve complete kill, i.e., a 5 or 6 log reduction, of the organisms tested. Even at a hydrogen peroxide concentration of 0.03 mg/cm$^2$ the time required to kill *B. subtilis* spores was 13 hours. This is a significantly smaller reaction time than the days required for other reactive surfaces.

Example 17—Increasing VHP Saturation

Consistent results were achieved with the 400 ppm, 30 minute VHP decontaminations cycle. Even so, it was thought that there was room to increase the initial concentration of the oxidant on the surface. Two tests were used to try and determine the maximum hydrogen concentration that the coating could sustain. One test looked at using the 400 ppm cycle with a longer exposure time; the other test looked at increasing the VHP exposure concentration to 1000 ppm.

Non-cross-linked films were prepared using 1300 K PVP in GC vial caps. Films were then exposed to either a 400 ppm or 1000 ppm VHP decontamination cycle for 2, 4 or 6 hours. All films were exposed to the conditioning phase and then recovered after the appropriate time of decontamination. Films were measured for total oxidant using a thiosulfate titration. All values were reported per surface area of exposure.

FIG. 24 shows the peroxide capacity levels of 1300 PVP films after extended and high VHP exposure. The hydrogen peroxide levels continued to increase at a steady rate for both the 400 ppm and 1000 ppm levels over the entire 6 hours. It appeared that even at a 6-hour decontamination phase at 1000 ppm, the PVP films could still absorb more peroxide. This result indicates the potential for significantly higher levels of peroxide to be loaded in to the system and could be used to modify the level of peroxide for different applications of the technology. The loading level offers the possibility for the activation level of the surfaces to be tailored for different threats including certain chemical agents. While chemical efficacy was not detected in NMR work at the 0.5 mg/cm$^2$ level, higher peroxide concentrations may offer better results.

Example 18—Activation Via Liquid Hydrogen Peroxide

Testing was performed to evaluate the impact of activating the films by exposure to vaporous or liquid hydrogen peroxide. A liquid application would provide a solution for spot decontamination or activation by spraying rather than sealing off an entire area for VHP exposure and could result in a faster and higher level of activation. There may be trade-offs, such as the labor required for application, safety and ability to reach all the surfaces. Even so, the ability to use either or both activation methods would provide flexibility to the user to best meet their immediate needs.

LDPE/PVP films were selected to compare the two activation methods as they had the lowest hydrogen peroxide uptake for VHP cycles and did not exhibit the same swelling or solubility issues seen when liquids were applied to cross-linked or non-cross-linked PVP films.

LDPE/PVP film samples were either exposed to a 400 ppm 30 minute VHP decontamination cycle or were submerged in a 7% hydrogen peroxide solution for 1, 5 or 10 minutes, then rinsed with milli-Q water and allowed to dry before testing. Hydrogen peroxide concentration was calculated per unit area and tested using a total oxidant thiosulfate titration method.

Figure 25:
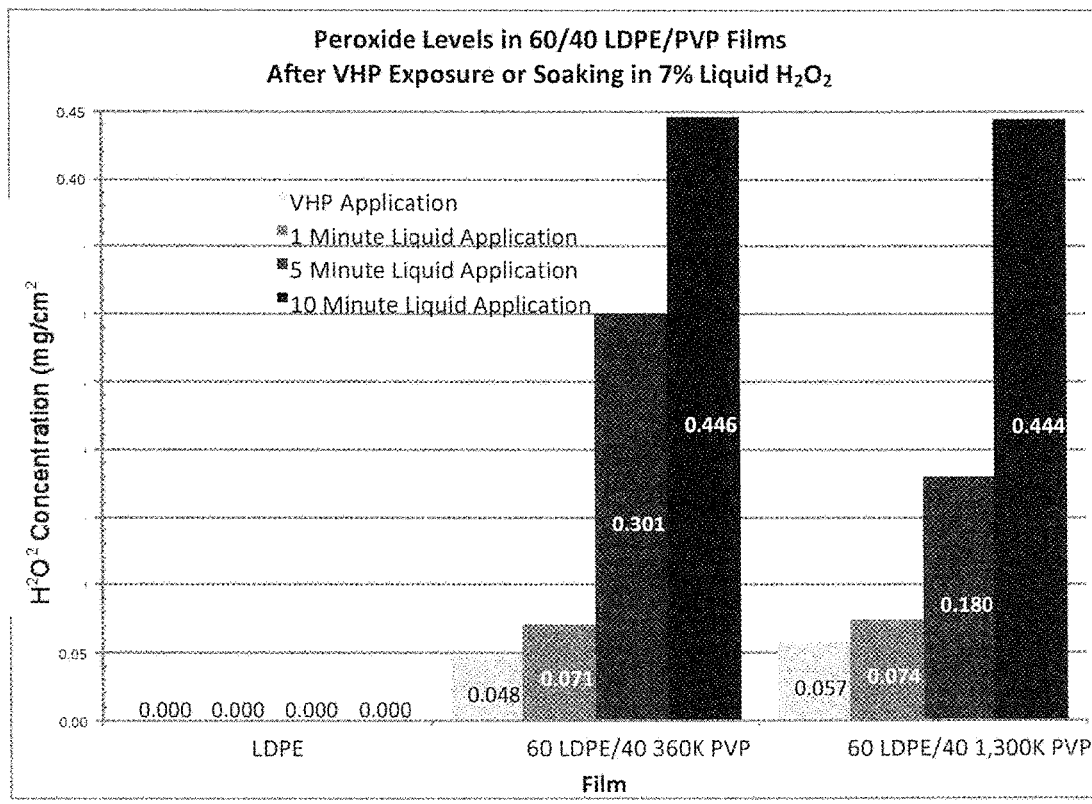
FIG. 25 reflects hydrogen peroxide concentration levels (mg/cm$^2$) of 60/40 LPPE/PVP films after VHP exposure or soaking in 7% liquid hydrogen peroxide.

FIG. 25 shows the test results achieved. The results indicate that a 1 minute soak of the 60LDPE/40PVP film provided a hydrogen peroxide level close to that of samples exposed to VHP. In addition, the extra time at 5 and 10 minutes gives increasing levels of hydrogen peroxide, with the 10 minute samples being equivalent to levels seen in cross-linked PVP after exposure to a typical VHP cycle. Note that lower concentrations of PVP incorporated into LDPE gave lower peroxide absorption values (data not shown).

This example shows that both liquid peroxide and VHP are viable activation techniques for the inventive technology. While liquid application appeared initially to provide a higher level of active on the coating, similar results can also be achieved by altering the VHP cycle exposure time and concentration. Application of a liquid to a PVP based coating, which is not cross-linked or otherwise formulated to limit solubility, would result in the removal of the coating and thus might be disadvantageous. Additionally, application of a large amount of liquid to cross-linked PVP surfaces induces swelling, another undesirable result. Even so, both techniques offer flexibility for activation options for the user.

Example 19—Safety Evaluation

The chemistries of the inventive compositions have a good safety profile. PVP and hydrogen peroxide are both commonly known for use in human applications and are very well characterized by a long use history. Hydrogen peroxide is commonly used at a 3% solution for the disinfection of wounds, but has the potential to generate injuries when used at >10%. OSHA also has guidelines for exposure to hydrogen peroxide vapors, which include a permissible exposure limit for VHP of one part per million (time weighted average over 8 hours). For this reason, a safety evaluation was performed to predict the amount of VHP that could be found in a typical room if the inventive coatings were applied to the walls and ceilings and then activated.

An 8 inch×8 inch glass slide was coated using a 10% 1300 K PVP solution in methanol and allowed to dry. The coating was then activated by exposure to a 400 ppm 30 minute VHP cycle and placed in a chamber with a volume of ~20 liters. The concentration of hydrogen peroxide in the headspace size was measured using a Draeger monitor at given intervals. These concentrations were then converted to a hypothetical concentration for an 18.8 ft.×14.8 ft.×9 ft. room in which all four walls and the ceiling would be coated and activated. The calculation was based on "no room ventilation" and thus presents the conservative case.

The results are shown in Table 3. The results provided an early indication that if a system made up of PVP were to be applied to the walls of a room and if the activation level with hydrogen peroxide was at 0.4-0.6 mg/cm2, the off-gassing of hydrogen peroxide in a room with no ventilation would not be unreasonably high. While this example is an approximation, the addition of even minor ventilation in the room would reasonably prevent the buildup of any hazardous vapors.

TABLE 3

Ambient VHF concentration from off-gassing over time

| Off-gas time | Ambient VHP concentration (ppm) |
|---|---|
| 2 Hours | 0.287 |
| 4 Hours | 0.430 |
| 24 Hours | 0.717 |
| 48 Hours* | 0.839* |
| 72 Hours (3 Days)* | 0.909* |
| 96 Hours (4 Days)* | 0.958* |
| 120 Hours (5 Days)* | 0.996* |

(* = calculated)

Accordingly, it was concluded that an activated reactive surface of the present invention were applied to the walls of a standard room, the levels of VHP in the room would not exceed the OSHA limit.

Example 20—Biological Interactions With PVP Crosslinked Film With Vaporous Hydrogen Peroxide Exposure The surfaces of the inventive films are highly hygroscopic. When an organism came in contact with the surface, the moisture surrounding the organism was drawn into contact with the surface providing two significant results. The first was that the organism was drawn into close contact with the active, thereby enhancing the efficacy of the surface. Secondly, the surface was essentially stirred by the movement of water within the film thereby minimizing the impact of surface contaminants moisture in the process.

A comparison was performed using TRIOSYN fabric. In the TRIOSYN coated fabric, the active was observed as discrete particles of material attached loosely to the fibers of the hydrophobic substrate fabric. When the inoculum was applied, the S. aureus cells were clearly visible and had a normal vibrating motion in a single location and no general movement towards the active ingredient.

Two significant observations were apparent. First, the surface of the film was highly uniform. It appeared by observation that the polymer was very evenly distributed and the active, while not visible, was evenly and microscopically distributed across the surface of the film. Second, there was an extremely high amount of movement of the *S. aureus* cells on the surface of the film. The inoculum appeared to be flowing at a fairly high rate as the surface absorbed moisture and along with it the cells.

After inoculation, it appeared as if the surface was flowing like a river taking the cells along with it in a stirring pattern. While not wishing to be bound by theory, it is postulated that this stirring motion, along with the uniformity of the active on the surface, significantly enhanced the efficacy of the system and helped to achieve the synergistic increase in efficacy at the same time as it resists fouling by organic loading.

Example 21—Effect of Organic Load

Figure 26:
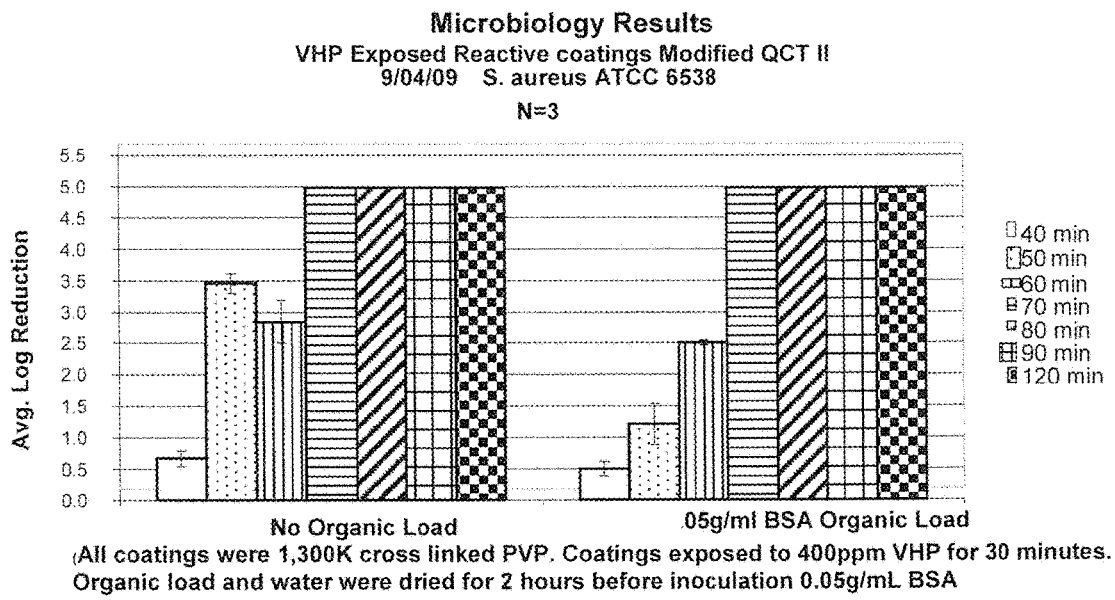
FIG. 26 reflects that organic load has no impact on the reactivity of the inventive surface against *S. aureus* ATCC 6538.

Concerns of fouling of the surface prompted a look at the effect of organic load on the reactivity of the surface. 0.5 g/mL of BSA (Bovine Serum Albumin) was the chosen level. 20 μL of this solution was applied to an activated film surface and allowed to dry in order to simulate build up of organic material on the surface over time. The surface was then tested in the same manner as all other surfaces. The data in FIG. 26 shows that this level of organic load had no impact on the reactivity of the surface against *S. aureus* as compared to the same activated surface with no organic load.

Example 22—Relevant Surfaces Testing

In the foregoing examples, PVP/HP reactive solutions were applied to many surfaces, by way of example, but not limited to, military and healthcare relevant surfaces such as tent materials, uniform fabrics, and painted surfaces (including the military relevant CARC (chemical agent resistant coating) paint). All surfaces tested behaved similarly in their acceptance of the hydrogen peroxide activator and in microbiological efficacy.

Example 23—Polyvinylpyrrolidone (PVP) with Solid Peroxides

Figure 27:
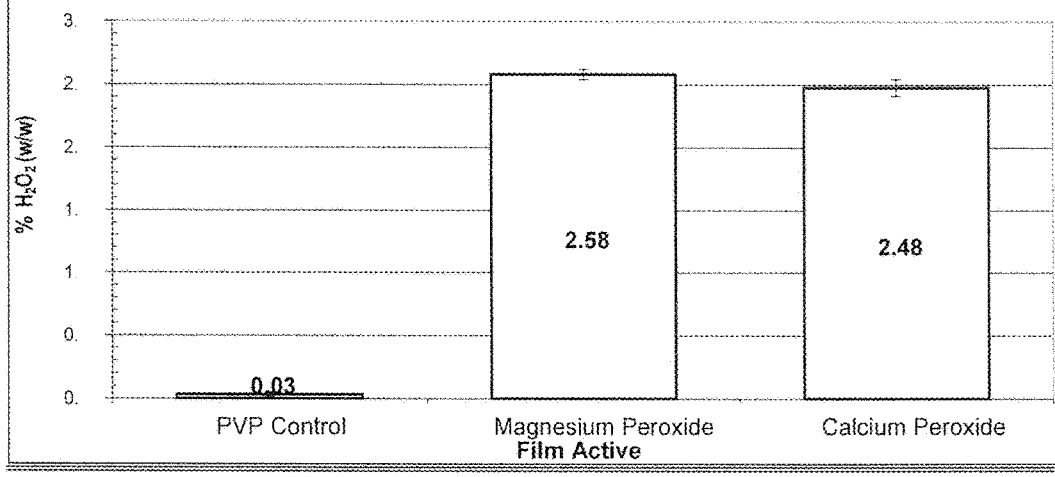
FIG. 27 reflects available oxidant (expressed as weight percent hydrogen peroxide) in 40%, 58 K PVP films using magnesium and calcium peroxide as film actives.
Figure 28:
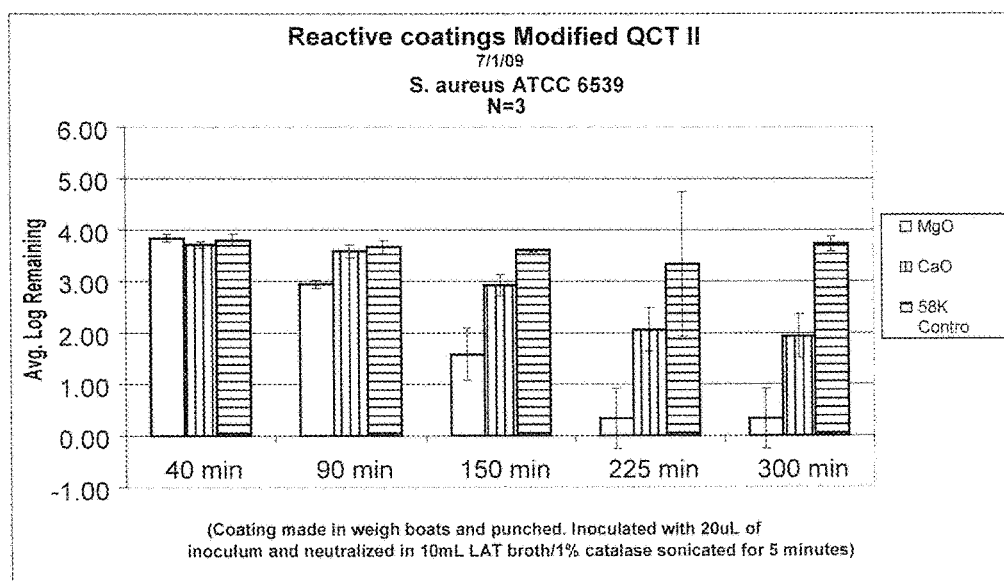
FIG. 28 reflects average log reductions of *S. aureus* ATCC 6538 by contact with 58 K PVP control and films having magnesium and calcium peroxide actives.

Solid additives, for example, calcium peroxide and magnesium peroxide, were combined with 58K PVP solutions and used to make films. These films contained approximately 3% peroxide by weight. See FIG. 27. Microbiological testing with *S. aureus* applied to the surface achieved a four log reduction in 300 minutes with magnesium peroxide. Calcium peroxide achieved a two log reduction in the same time frame. See FIG. 28. The microbiological test method for these samples was identical to the previously described surface testing.

In accordance with the patent statutes, the best mode and preferred embodiment have been set forth; the scope of the invention is not limited thereto, but rather by the scope of the attached claims.

What is claimed is:

1. A method for providing a renewable reactive film coating, having biocidal and chemical decontamination properties against biological and chemical warfare agents, to a surface of an object or article, consisting of the steps of:
   a. applying a hygroscopic polymer solution to the surface of the object or article, wherein the polymer consists of non-cross-linked, water soluble polyvinylpyrrolidone, dissolved in (i) water or (ii) water and methanol to form a solution, wherein the polyvinylpyrrolidone has a molecular weight of 10K, 58K, 360K or 1300K and is present in an amount ranging from about 1 to about 10 wt. %, based on the total weight of the renewable reactive film coating;
   b. processing the polymer solution to form a film;
   c. exposing the film to an initial charge of an oxidant consisting of hydrogen peroxide, wherein the hydrogen peroxide is provided as: i) an aqueous solution of hydrogen peroxide present in an amount ranging from about 10-20 wt. %, or ii) vaporized hydrogen peroxide of at least about 400 ppm of vaporized hydrogen peroxide for a time of about 30 minutes;
   d. air drying the film, and
   e. renewing the biocidal and chemical decontamination properties of the film, after fouling, or exhaustion or decay of the hydrogen peroxide active due to contact with biological or chemical warfare agents, by exposing the film to additional vaporized hydrogen peroxide.

2. A method of providing a renewable reactive film coating, having biocidal and chemical deactivation properties against biological and chemical warfare agents, to the surface of an object or article, consisting of the steps of:
   a. providing a solution consisting of i) a non-cross-linked, water soluble polyvinylpyrrolidone dissolved in water, or ii) a non-crosslinked, water soluble polyvinylpyrrolidone dissolved in water and methanol, wherein the polyvinylpyrrolidone has a molecular weight of 10K, 58K, 360K or 1300K and is present in an amount ranging from about 1 to about 10 wt. %, based on the total weight of the renewable reactive film coating;
   b. mixing the polyvinylpyrrolidone solution with an active consisting of aqueous solution of hydrogen peroxide to form a mixture, wherein the aqueous hydrogen peroxide solution is a 10 wt. % or 20 wt. % solution;
   c. applying the mixture to the surface of the object or article;
   d. drying the mixture in air to form a film; and,
   e. renewing the biocidal and chemical decontamination properties of the film, after fouling, or exhaustion or decay of the hydrogen peroxide active due to contact with biological or chemical warfare agents, by exposing the film to vaporized hydrogen peroxide of at least about 400 ppm for at least 30 minutes.

3. A method of providing a renewable reactive film coating, having biocidal and chemical deactivation properties against biological and chemical warfare agents, to the surface of an object or article, consisting of the steps of:
   a. providing a solution consisting of i) a non-cross-linked, water soluble polyvinylpyrrolidone dissolved in water, or ii) a non-crosslinked, water soluble polyvinylpyrrolidone dissolved in water and methanol, wherein the polyvinylpyrrolidone has a molecular weight of 10K, 58K, 360K or 1300K and is present in an amount ranging from about 1 to about 10 wt. %, based on the total weight of the renewable reactive film coating;
   b. mixing the polyvinylpyrrolidone solution with an active consisting of peracetic acid or iodine to form a mixture, wherein the active is present in an amount ranging from about 1 to about 10 wt. %, based on the total weight of the renewable reactive film coating;
   c. applying the mixture to the surface of the object or article;
   d. drying the mixture in air to form a film; and,
   e. renewing the biocidal and chemical decontamination properties of the film, after fouling, or exhaustion or decay of the active due to contact with biological or chemical warfare agents, by exposing the film to additional amounts of the active.

4. A method for providing a renewable reactive film coating, having biocidal and chemical decontamination properties against biological and chemical warfare agents, to a surface of an object or article, consisting of the steps of:
   a. applying a hygroscopic polymer solution to the surface of the object or article,
   wherein the polymer consists of non-cross-linked, water soluble polyvinylpyrrolidone, dissolved in (i) water or (ii) water and methanol to form a solution, wherein the polyvinylpyrrolidone has a molecular weight of 10K, 58K, 360K or 1300K and is present in an amount ranging from about 1 to about 10 wt. %, based on the total weight of the renewable reactive film coating;
   b. processing the polymer solution to form a film;
   c. exposing the film to an initial charge of an active consisting of chlorine gas;
   d. air drying the film; and
   e. renewing the biocidal and chemical decontamination properties of the film, after fouling, or exhaustion or decay of the active due to contact with biological or chemical warfare agents, by exposing the film to additional amounts of chlorine gas.

\* \* \* \* \*